US011174289B1

(12) United States Patent
Das et al.

(10) Patent No.: US 11,174,289 B1
(45) Date of Patent: Nov. 16, 2021

(54) ARTIFICIAL INTELLIGENCE DESIGNED ANTIMICROBIAL PEPTIDES

(71) Applicants: International Business Machines Corporation, Armonk, NY (US); Agency for Science, Technology and Research, Singapore (SG)

(72) Inventors: Payel Das, Yorktown Heights, NY (US); Flaviu Cipcigan, Warrington (GB); James L. Hedrick, Pleasanton, CA (US); Yi Yan Yang, Singapore (SG); Kahini Wadhawan, Ferozepur (IN); Inkit Padhi, White Plains, NY (US); Enara C Vijil, Millwood, NY (US); Pang Kern Jeremy Tan, Singapore (SG)

(73) Assignees: INTERNATIONAL BUSINESS MACHINES CORPORATION, Armonk, NY (US); AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 0 days.

(21) Appl. No.: 16/880,280

(22) Filed: May 21, 2020

(51) Int. Cl.
*A61K 38/10* (2006.01)
*C07K 7/08* (2006.01)
*A61K 38/00* (2006.01)

(52) U.S. Cl.
CPC ................ *C07K 7/08* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 2011/0161265 | A1 | 6/2011 | Gustafsson et al. |
| 2011/0236429 | A1 | 9/2011 | Hancock et al. |
| 2013/0252280 | A1 | 9/2013 | Weaver et al. |
| 2015/0142408 | A1 | 5/2015 | Futamura |
| 2017/0161635 | A1 | 8/2017 | Oono et al. |
| 2019/0010533 | A1 | 1/2019 | Wong |
| 2019/0018933 | A1 | 1/2019 | Oono et al. |
| 2019/0252036 | A1 | 8/2019 | Elemento et al. |
| 2019/0304568 | A1 | 10/2019 | Wei et al. |
| 2019/0362816 | A1 | 11/2019 | Statsyuk |
| 2019/0392304 | A1 | 12/2019 | Aliper et al. |
| 2020/0020415 | A1 | 1/2020 | Sarmiento et al. |

FOREIGN PATENT DOCUMENTS

| | | | |
|---|---|---|---|
| CN | 110317248 | A | 10/2019 |
| CN | 111081316 | A | 4/2020 |
| WO | 2018220368 | A1 | 12/2018 |
| WO | 2019081781 | A1 | 5/2019 |

OTHER PUBLICATIONS

French, Simon and Robson, Barry; "What is a conservative substitution?" J. Mol. Evol. (1983) 19:171-175.*

CAS Registry: Exact and pattern searching of protein sequences (2008).*

Maraj, Rajiv et al; "Evaluation of hemolysis in patients with prosthetic heart valves." Clin. Cardiol. (1998) 21 p. 387-392.*

Phoenix, David A. and Harris, Frederick; "The hydrophobic moment and its use in the classification of amphiphilic structures." Mol. Membrane Biol. (2002) 19 1-10.*

Yampolsky, Lev Y. and Stoltzfus, Arlin; "The exchangeability of amino acids in proteins." Genetics (2005) 1459-1472.* amr-review.org,, "Review on Antimicrobial Resistance," Retrieved from the Internet: Mar. 17, 2020, https://amr-review.org/, 2 pages.

Mourtada, et al., "Design of stapled antimicrobial peptides that are stable, nontoxic and kill antibiotic-resistant bacteria in mice," Nat Biotechnol 37, pp. 1186-1197, 2019.

Das et al., "PepCVAE: Semi-Supervised Targeted Design of Antimicrobial Peptide Sequences," (Submitted on Oct. 17, 2018 (v1), last revised Nov. 13, 2018 (this version, v3), https://arxiv.org/abs/1810.07743.

Mondal, "A brief appraisal of computational modeling of antimicrobial peptides' activity." Drug Dev Res., vol. 80, No. 1., pp. 28-32, Feb. 2019.

Müller et al., "Recurrent Neural Network Model for Constructive Peptide Design." J. Chem. Inf. Model., 58, 2, pp. 472-479, 2018.

Witten, "Deep learning regression model for antimicrobial peptide design." bioRxiv 692681, Posted Jul. 12, 2019. https://www.biorxiv.org/content/10.1101/692681v1.abstract.

Nagarajan, et al., "Computational antimicrobial peptide design and evaluation against multidrug-resistant clinical isolates of bacteria," JBC Papers in Press. Published on Dec. 19, 2017 as Manuscript M117.805499, http://www.ibc.org/cgi/doi/10.1074/jbc.M117.805499.

Mell et al. "The NIST Definition of Cloud Computing." National Institute of Standards and Technology, Sep. 2011, 7 pages.

List of IBM Patents or Applications Treated as Related, Jun. 18, 2020.

Kingma et al., "Auto-Encoding Variational Bayes" arXiv:1312.6114v10m, May 1, 2014, 14 pages.

Bowman et al., "A large annotated corpus for learning natural language inference", arXiv:1508.05326, Aug. 21, 2015, 11 pages.

Hochreiter et al., "Long Short-Term Memory", Neural computation vol. 9, No. 1, 1997, pp. 32.

(Continued)

*Primary Examiner* — Fred H Reynolds
(74) *Attorney, Agent, or Firm* — Amin, Turocy & Watson, LLP

(57) ABSTRACT

De novo, artificial intelligence (AI) designed antimicrobial peptides (AMPs), antibacterial products comprising the AMPs and methods for treating bacterial infections using the products are provided. In one or more embodiments, the AMPs were designed using conditional latent attribute space sampling (CLaSS). The AMPs comprise up to twenty natural amino acids in length, including one with twelve and another with thirteen natural amino acids in length. The AMPs demonstrate low-toxicity and show high antimicrobial potency against diverse pathogens including multi-medication-resistant Gram negative *Klebsiella pneumoniae.*

15 Claims, 12 Drawing Sheets

Specification includes a Sequence Listing.

(56) References Cited

OTHER PUBLICATIONS

Bowman et al., "Generating Sentences from a Continuous Space", arXiv preprint arXiv:1511.06349, May 12, 2015, 12 pages.
Tolstikhin et al.,"Wasserstein Auto-Encoders", arXiv preprint arXiv:1711.01558, Dec. 5, 2017, 20 pages.
Bahuleyan et al., "Stochastic Wasserstein Autoencoder for Probabilistic Sentence Generation" arXiv:1806.08462, Apr. 12, 2018, 9 pages.
Makhzani et al., "Adversarial Autoencoders" arXiv:1511.05644, May 25, 2015, 16 pages.
Gretton et al., "A Kernel Method for the Two-Sample-Problem", Advances in neural information processing systems, 2007, 8 pages.
Rahimi et al., "Unsupervised Regression with Applications to Nonlinear System Identification", Advances in neural information processing systems, 2007, 8 pages.
Rubenstein et al., "On the Latent Space of Wasserstein Auto-Encoders", arXiv:1802.03761 , Feb. 11, 2018, 9 pages.
Theis et al., "A Note on The Evaluation of Generative Models", ICLR, Apr. 24, 2016, 10 pages.
Alemi, et al.,"Fixing a Broken ELBO" arXiv:1711.00464, Feb. 13, 2017, 21 pages.
Ranzato et al., "Sequence Level Training with Recurrent Neural Networks", arXiv preprint arXiv:1511.06732, May 6, 2015, 16 pages.
Bengio et al., "Scheduled Sampling for Sequence Prediction with Recurrent Neural Networks", Advances in Neural Information Processing Systems, 2015, 9 pages.
Zhao et al., "Adversarially Regularized Autoencoders", arXiv:1706.04223, Jun. 29, 2017, 16 pages.
Merity et al., "Regularizing and Optimizing LSTM Language Models", arXiv preprint arXiv:1708.02182, Aug. 7, 2017, 10 pages.
Yu et al., "SeqGAN: Sequence Generative Adversarial Nets with Policy Gradient",Thirty-First AAAI Conference on Artificial Intelligence, 2017, pp. 2852-2858.
Guimaraes et al., ,"Objective-Reinforced Generative Adversarial Networks (ORGAN) for Sequence Generation Models" arXiv preprint arXiv:1705.10843, Feb. 7, 2017, 7 pages.
Jang et al., "Categorical Reparameterization with Gumbel-Softmax", arXiv:1611.01144, Aug. 5, 2017, 13 pages.
Kusner et al., "GANS for Sequences of Discrete Elements with the Gumbel-softmax Distribution", arXiv:1611.04051, Nov. 12, 2016, 6 pages.
Maddison et al., "The Concrete Distribution: A Continuous Relaxation of Discrete Random Variable", arXiv:1611.00712, Mar. 5, 2017, 20 pages.
Zhang et al., "Generating Text via Adversarial Training", Workshop on Adversarial Training, NIPS 2016, Barcelona, Spain, 2016, 6 pages.
Kingma et al., "Semi-supervised Learning with Deep Generative Models", Advances in Neural Information Processing Systems, 2014, 9 pages.
Hu et al., "Toward Controlled Generation of Text", International Conference on Machine Learning, 2017, 10 pages.
Engel et al., "Latent Constraints: Learning To Generate Conditionally From Unconditional Generative Models", Dec. 21, 2017, arXiv:1711.05772, 22 pages.
Dathathri et al., "Plug and Play Language Models: A Simple Approach To Controlled Text Generation", arXiv preprint arXiv:1912.02164, Mar. 3, 2020, 34 pages.
Bombarelli et al., "Automatic Chemical Design Using a Data-Driven Continuous Representation of Molecules", ACS central science, vol. 4, Jun. 14, 2018, pp. 268-276.
Zhou et al., "Optimization of Molecules via Deep Reinforcement Learning", Scientific reports, vol. 9, Jul. 24, 2019, 10 pages.
You et al., "Graph Convolutional Policy Network for Goal-Directed Molecular Graph Generation" Advances in Neural Information Processing Systems, 2018, 12 pages.
Popova et al., "Deep reinforcement learning for de novo drug design", Science advances , Jul. 26, 2018, vol. 4, 15 pages.
Zhavoronkov et al., "Deep learning enables rapid identification of potent DDR1 kinase inhibitors", Nature Biotechnology, vol. 37, Sep. 2019, pp. 1038-1046.
Korovina et al., "ChemBO: Bayesian Optimization of Small Organic Molecules with Synthesizable Recommendations" arXiv:1908.01425v2, Oct. 22, 2019, 19 pages.
Lim et al., "Molecular generative model based on conditional variational autoencoder for denovo molecular design", vol. 10. No. 31, 2018, 9 pages.
Kang et al., "Conditional molecular design with deep generative models", Journal of chemical information and modeling, vol. 59, No. 43, Jul. 18, 2018, 27 pages.
Li et al., "Multi-objective de novo drug design with conditional graph generative model", vol. 10, No. 33, 2018, 24 pages.
Sib S, Universal Protein Resource (UniProt), https://www.uniprot.org, (2018) 2 pages.
Singh et al., "SATPdb: a database of structurally annotated therapeutic peptides", Nucleic acids research, Nov. 2, 2015, pp. 1119-1126.
Pirtskhalava et al.,"DBAASP v.2: an enhanced database of structure and antimicrobial/cytotoxic activity of natural and synthetic peptides" Nucleic acids research, vol. 44, 2015, p. 1104 1112.
Khurana et al., "DeepSol: a deep learning framework for sequence-based protein solubility prediction" Bioinformatics, vol. 34, No. 15, Mar. 15, 2018, pp. 2605-2613.
Bhadra et al., "AmPEP: Sequence-based prediction of antimicrobial peptides using distribution patterns of amino acid properties and random forest", Scientific reports, Jan. 26, 2018, 10 pages.
Gupta et al., "In Silico Approach for Predicting Toxicity of Peptides and Proteins", PloS one, vol. 8, No. 9, Sep. 2013, 10 pages.
Frishman et al., "Knowledge-Based Protein Secondary Structure Assignment", Proteins: Structure, Function, and Genetics vol. 23, 1995, pp. 566-579.
Tien et al., "PeptideBuilder: A simple Python library to generate model peptides", Peerj, May 21, 2013, 10 pages.
Jong et al., "Improved Parameters for the Martini Coarse-Grained Protein Force Field", Journal of Chemical Theory and Computation, Jul. 25, 2012, 11 pages.
Wassenaar et al., "Computational Lipidomics with insane: A Versatile Tool for Generating Custom Membranes for Molecular Simulations", Journal of Chemical Theory and Computation, Apr. 10, 2015, pp. 2144-2155.
Marrink et al., "The Martini Force Field: Coarse Grained Model for Biomolecular Simulations", The Journal of Physical Chemistry, vol. 111, Apr. 25, 2007, pp. 7812-7824.
Berendsen et al., "GROMACS: A message-passing parallel molecular dynamics implementation", Computer Physics Communications vol. 91, Dec. 2, 1994, pp. 43-56.
Abraham et al., "GROMACS: High performance molecular simulations through multi-level parallelism from laptops to supercomputers", SoftwareX 1-2, Jun. 25, 2015, 7 pages.
Bussi et al., "Canonical sampling through velocity rescaling", The Journal of Chemical Physics, vol. 126, Jan. 3, 2007, 8 pages.
Rahman et al., "Polymorphic transitions in single crystals: A new molecular dynamics method", Journal of Applied Physics vol. 52, Aug. 14, 1981, pp. 7182-7190.
Nose et al., "Constant pressure molecular dynamics for molecular systems", Molecular Physics vol. 50, 1983, pp. 1055-1076.
Huang et al., "CHARMM 36m: an improved force field for folder and intrinsically disordered proteins", Nov. 7, 2016, Nature Methods, vol. 14, 6 pages.
Qin et al., "Artificial intelligence method to design and fold alphahelical structural proteins from the primary amino acid sequence", Extreme Mechanics Letters, 2020, 26 pages.
Jo et al., "CHARMM-GUI Membrane Builder for Mixed Bilayers and Its Application to Yeast Membranes", Biophysical Journal vol. 97, Jul. 2009, 50-58 pp.
Humphrey et al., "VMD: Visual Molecular Dynamics", Journal of Molecular Graphics, vol. 14, Feb. 1996, pp. 33-38.
Phillips et al., "Scalable Molecular Dynamics with NAMD", May 26, 2005, pp. 1781-1802.
Muller et al., "modlAMP: Python for antimicrobial peptides", Bioinformatics, vol. 33, No. 17, 2017, pp. 2753-2755.

(56) References Cited

OTHER PUBLICATIONS

Yu et al.,The compositional adjustment of amino acid substitution matrices, Proceedings of the National Academy of Sciences, vol. 100, No. 26, Dec. 23, 2003, 15688-15693.
Cock et al., "Biopython: freely available Python tools for computational molecular biology and bioinformatics", Bioinformatics vol. 25, No. 11 Mar. 20, 2009, pp. 1422-1423.
Madden, Thomas., "The BLAST Sequence Analysis Tool", The NCBI Handbook [Internet]. 2nd edition (National Center for Biotechnology Information (US), Mar. 15, 2013, 10 pages.
Chin et al., "A macromolecular approach to eradicate multidrug resistant bacterial infections while mitigating drug resistance onset", Nature communications, vol. 9, No. 1, 2018, 14 pages.
Ng et al., "Synergistic Co-Delivery of Membrane-Disrupting Polymers with Commercial Antibiotics against Highly Opportunistic Bacteria", Advanced Materials, vol. 25, 2013, pp. 6730-3736.
Liu et al., "Highly potent antimicrobial polyionenes with rapid killing kinetics, skin biocompatibility and in vivo bactericidal activity", Biomaterials, vol. 127, Feb. 28, 2017, pp. 36-48.
Li, et al. "Multi-objective de novo drug design with conditional graph generative model" J Cheminform (2018) 10:33, https://jcheminf.biomedcentral.com/track/pdf/10.1186/s13321-018-0287-6. 24 pages.
International Search Report and Written Opinion received for PCT Application Serial No. PCT/IB2021/054139 dated Aug. 24, 2021, 12 pages.

* cited by examiner

Broad Spectrum Minimum Inhibitory Concentrations (MICs) for the Top 20 Candidate Antimicrobial Peptides (AMPs)

| | Sequence | S. aureus (μg/mL) | E.Coli (μg/mL) |
|---|---|---|---|
| SEQ ID NO: 1(YI12) -CONH2 | YLRLIRYMAKMI-CONH2 | 7.8 | 31.25 |
| SEQ ID NO: 2(FK13) -CONH2 | FPLTWLKWWKWKK-CONH2 | 15.6 | 31.25 |
| SEQ ID NO: 3 -CONH2 | HILRMRIRQMMT-CONH2 | >1000 | >1000 |
| SEQ ID NO: 4 -CONH2 | ILLHAILGVRKKL-CONH2 | 250 | 250 |
| SEQ ID NO: 5 -CONH2 | YRAAMLRRQYMMT-CONH2 | >1000 | >1000 |
| SEQ ID NO: 6 -CONH2 | HIRLMRIRQMMT-CONH2 | >1000 | >1000 |
| SEQ ID NO: 7 -CONH2 | HIRAMRIRAQMMT-CONH2 | >1000 | 1000 |
| SEQ ID NO: 8 -CONH2 | KTLAQLSAGVKRWH-CONH2 | >1000 | >1000 |
| SEQ ID NO: 9 -CONH2 | HILRMRIRQGMMT-CONH2 | >1000 | >1000 |
| SEQ ID NO: 10 -CONH2 | HRAIMLRIRQMMT-CONH2 | >1000 | >1000 |
| SEQ ID NO: 11 -CONH2 | EYLIEVRESAKMTQ-CONH2 | >1000 | >1000 |
| SEQ ID NO: 12 -CONH2 | GLITMLKVGLAKVQ-CONH2 | >1000 | >1000 |
| SEQ ID NO: 13 -CONH2 | YQLLRIMRINIA-CONH2 | >1000 | >1000 |
| SEQ ID NO: 29 | VRWIEYWREKWRT-CONH2 | >1000 | >1000 |
| SEQ ID NO: 16 -CONH2 | YQLRLIMKYAI-CONH2 | 125 | 125 |
| SEQ ID NO: 17 -CONH2 | HRALMRIRQCMT-CONH2 | 1000 | 1000 |
| SEQ ID NO: 18 -CONH2 | GWLPTEKWRKLC-CONH2 | 1000 | >1000 |
| SEQ ID NO: 19 -CONH2 | YQLRLMRIMSRI-CONH2 | 250 | 500 |
| SEQ ID NO: 30 | FFPLPAISTELKRL-CONH2 | >1000 | >1000 |
| SEQ ID NO: 14 -CONH2 | LIQVAPLGRLLKRR-CONH2 | >1000 | 1000 |
| SEQ ID NO: 20 -CONH2 | LRPAFKVSK-CONH2 | >1000 | >1000 |

Table 500

FIG. 5

Broad-spectrum Antimicrobial Activity and Toxicity of YI12 (SEQ ID NO: 1) and FK13 (SEQ ID NO: 2)

| Sequence | S. aureus (µg/ml) | E. coli (µg/ml) | P. aeruginosa (µg/ml) | A. baumannii (µg/ml) | MDR K. pneumoniae (µg/ml) | $HC_{50}$ (µg/ml) | $LD_{50}$ (mg/kg) |
|---|---|---|---|---|---|---|---|
| YLRLIRYMAKMI-CONH2 (YI12 – SEQ ID NO: 1) | 7.8 | 31.25 | 125 | 15.6 | 31.25 | 125 | 182 |
| FPLTWLKWWKWKK-CONH2 (FK13 – SEQ ID NO: 2) | 15.6 | 31.25 | 62.5 | 31.25 | 15.6 | 500 | 158 |

Table 600

FIG. 6

Blast search results of YI12 (SEQ ID NO: 1) against 223.5 M Uniprot sequences

>WP_027115309.1 EAL domain-containing protein [Lachnospiraceae bacterium P6B14]

Length=643

Score = 33.3 bits (71), Expect = 2.9 , Coverage= 11/12 (91.6%)

Identities = 9/12 (75%), Positives = 10/12 (83%), Gaps = 1/12 (8%)

```
Query 1   YLRLIRYM-AKM 11
          YLR+IRYM  KM
Sbjct 353 YLRMIRYMESKM 364
```

FIG. 8A

Blast search results of FK13 (SEQ ID NO: 2) against 0.18 M training sequences

>Synthetic variant of PIN-A segment of Puroindoline-A

Length=13

Score = 33.3 bits (71), Expect = 1e-06, Coverage= 11/13 (84.6%)

Identities = 8/11 (73%), Positives = 8/11 (73%), Gaps = 1/11 (9%)

```
Query  1   FPLTWLKWWKW  11
           FPLTW  WWKW
Sbjct  1   FPLTW-RWWKW  10
```

FIG. 8B

ARTIFICIAL INTELLIGENCE DESIGNED ANTIMICROBIAL PEPTIDES

TECHNICAL FIELD

This application relates to artificial intelligence (AI) designed antimicrobial peptides (AMPs), antibacterial products comprising the AMPs and methods for treating bacterial infections using the products.

SUMMARY

The following presents a summary to provide a basic understanding of one or more embodiments of the present disclosure. This summary is not intended to identify key or critical elements or to delineate any scope of the particular embodiments or any scope of the claims. Its sole purpose is to present concepts in a simplified form as a prelude to the more detailed description that is presented later. In one or more embodiments described herein, de novo, AI-designed AMPs, antibacterial products comprising the AMPs and methods for treating bacterial infections using the products are provided. In one or more embodiments, the AMPs were designed using conditional latent attribute space sampling (CLaSS). The AMPs comprise up to twenty natural amino acids in length, including one with twelve and another with thirteen natural amino acids in length. The AMPs demonstrate low-toxicity and show high antimicrobial potency against diverse pathogens including multi-medication-resistant Gram negative *Klebsiella pneumoniae*.

According to an embodiment, a synthetic peptide (referred to herein as YI12) is provided that comprises twelve, natural amino acids in length and the amino acid sequence YLRLIRYMAKMI (SEQ ID NO: 1) or conservatively modified variants thereof, wherein the synthetic peptide has antimicrobial activity. In some implementations, the synthetic peptide YI12 further comprises a terminal amide with formula CONH2, resulting in the synthetic peptide having the sequence YLRLIRYMAKMI-CONH2.

In another embodiment, a synthetic peptide (referred to herein as FK13) is provided that comprises thirteen, natural amino acids in length and the amino acid sequence FPLTWLKWWKWKK (SEQ ID NO: 2) or conservatively modified variants thereof, wherein the synthetic peptide has antimicrobial activity. In some implementations, the synthetic peptide FK13 further comprises a terminal amide with formula CONH2, resulting in the synthetic peptide having the sequence FPLTWLKWWKWKK-CONH2.

In another embodiment, one or more synthetic peptides are provided that comprise up to twenty natural amino acids in length that were designed using conditional latent attribute space sampling (CLaSS). In some implementations, the one or more synthetic peptides comprise an amino acid sequence selected from the group consisting of: YLRLIRYMAKMI (SEQ ID NO: 1), FPLTWLKWWKWKK (SEQ ID NO: 2), HILRMRIRQMMT (SEQ ID NO: 3), ILLHAILGVRKKL (SEQ ID NO: 4), YRAAMLRRQYMMT (SEQ ID NO: 5), HIRLMRIRQMMT (SEQ ID NO: 6), HIRAMRIRAQMMT (SEQ ID NO: 7), KTLAQLSAGVKRWH (SEQ ID NO: 8), HILRMRIRQGMMT (SEQ ID NO: 9), HRAIMLRIRQMMT (SEQ ID NO: 10), EYLIEVRESAKMTQ (SEQ ID NO: 11), GLITMLKVGLAKVQ (SEQ ID NO: 12), YQLLRIMRINIA (SEQ ID NO: 13), LIQVAPLGRLLKRR (SEQ ID NO: 14), LIQVAPLGRLLKRR (SEQ ID NO: 15), YQLRLIMKYAI (SEQ ID NO: 16), HRALMRIRQCMT (SEQ ID NO: 17), GWLPTEKWRKLC (SEQ ID NO: 18), YQLRLMRIMSRI (SEQ ID NO: 19), LRPAFKVSK (SEQ ID NO: 20), and conservatively modified variants thereof. The one or more synthetic peptides further exhibit antimicrobial activity.

Also provided are antimicrobial products and pharmaceutical formulations comprising an any one or more of the synthetic peptides and/or AMPs described herein and a pharmaceutically acceptable excipient. In certain embodiments the formulation is a unit dosage formulation. In certain embodiments the excipient is acceptable for administration to an oral mucosa. In various implementations, the antimicrobial products/pharmaceutical formulations are effective against Gram positive bacteria and Gram negative bacteria, including MDR *K. pneumonia, P. aeruginosa, A. baummannii, S. aureus*, and *E. coli.*

Also provided are methods of inhibiting the growth and/or proliferation of a bacterium (or other pathogens). The methods typically involve contacting the bacterium or other pathogen with one or more of the synthetic peptides and/or AMPs described herein, in an amount sufficient to inhibit growth and/or proliferation of the bacterium or other pathogen. In certain embodiments the amount is an amount sufficient to exterminate the bacterium/pathogen. In certain embodiments the bacterium can comprise a Gram positive bacterium and/or a Gram negative bacterium, including (but not limited to): MDR *K. pneumonia, P. aeruginosa, A. baummannii, S. aureus*, and *E. coli.*

DESCRIPTION OF THE DRAWINGS

FIG. 5 provides a table illustrating the minimum inhibitory concentrations of the top 20 candidate AMPs against *S. aureus* and *E. coli.*

FIG. 6 provides a table illustrating the broad-spectrum antimicrobial activity and toxicity of YI12 (SEQ ID NO: 1) and FK13 (SEQ ID NO: 2).

FIGS. 8A and 8B present the basic local alignment search tool (BLAST) search results of YI12 (SEQ ID NO: 1) and FK13 (SEQ ID NO: 2), respectively.

DETAILED DESCRIPTION

Figure 1:
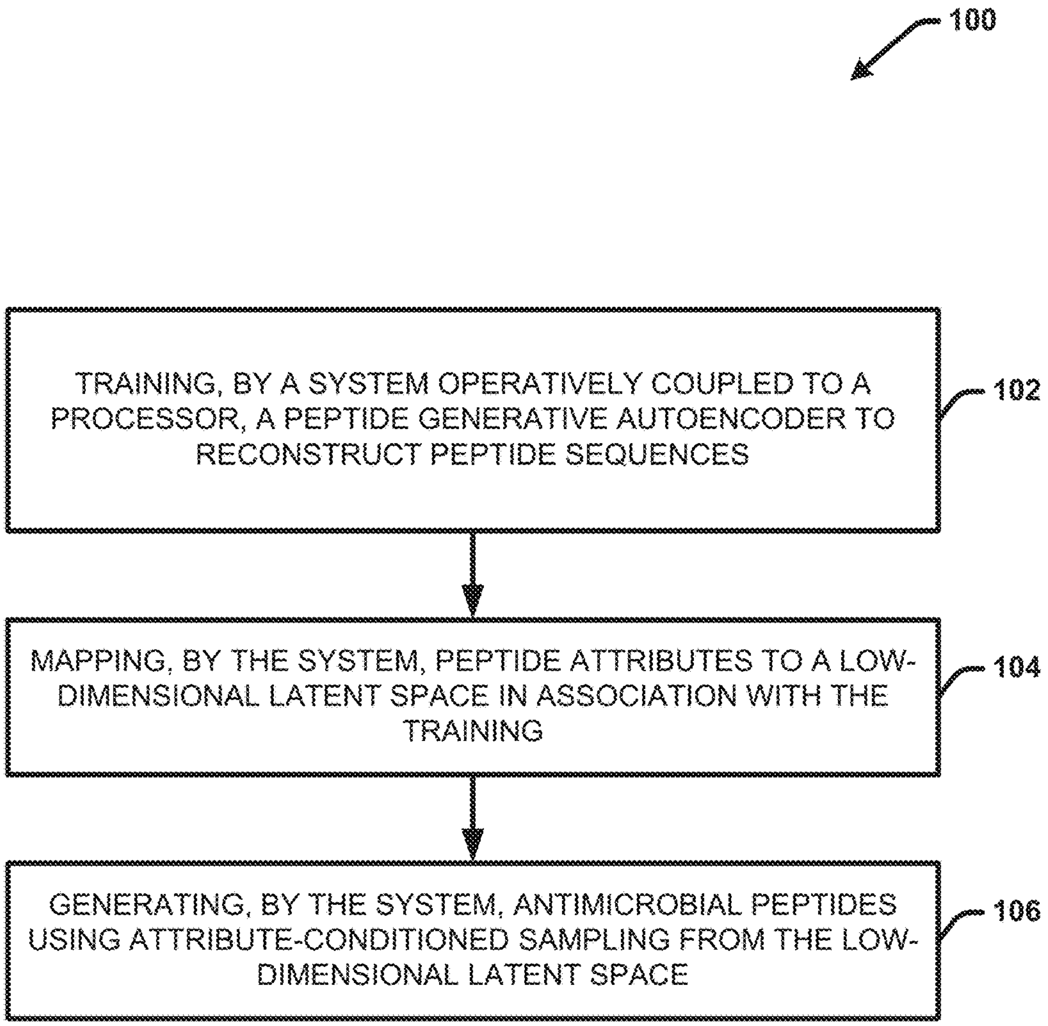
FIG. 1 provides a high-level flow diagram of an example computer-implemented method for AMP design using deep generative models and controllable sampling, in accordance with one or more embodiments of the disclosed subject matter.

The following detailed description is merely illustrative and is not intended to limit embodiments and/or application or uses of embodiments. Furthermore, there is no intention to be bound by any expressed or implied information presented in the preceding Technical Field or Summary sections, or in the Detailed Description section.

The disclosed subject matter provides AI-designed AMPs that capture the high selectivity of natural AMPs, providing maximum antimicrobial activity, while minimizing toxicity toward the host. In particular, the disclosed subject matter provides synthetic AMPs that are designed using deep generative models empowered with controllable sampling and physics-driven simulations. In one or more embodiments, the disclosed AI-designed AMPs comprise peptides with amino acids sequences of about 10 to 20 natural amino acids that were designed using a conditional latent (attribute) space sampling (CLaSS) method, followed by screening using deep learning classifiers augmented with molecular simulations.

The disclosed subject matter further provides novel AI-designed AMPs that were designed using the CLaSS method. The disclosed AI-designed AMPs provide broad-spectrum antimicrobial activity and low toxicity with a minimalist sequence structure. In particular, the novel AMPs have short amino acid sequences (e.g., about 20 or less natural amino acid characters), including one with 12 amino acids referred to herein as YI12, and another with 13 amino acids, referred to herein as FK1. The amino acid sequence of YI12 is YLRLIRYMAKMI (SEQ ID NO: 1), and the amino acid sequence of FK13 is FPLTWLKWWKWKK (SEQ ID NO: 2). Owing to their short sequence structure, these AMPs exhibit high peptide stability, and low synthesis costs. Both peptides are positively charged and have a nonzero hydrophobic moment, indicating their cationic amphiphilic nature in line with known antimicrobials. Both of these novel AMPs demonstrate high antimicrobial potency against diverse pathogens including multi-medication-resistant gram-negative *Klebsiella pneumonia* (*K. pneumonia*), as well as gram negative *Pseudomonas aeruginosa* (*P. aeruginosa*), gram-negative *Acinetobacter* baummannii (*A. baummannii*), gram-positive *Staphylococcus aureus* (*S. aureus*), and gram-negative *Escherichia coli* (*E. coli*).

Both of these AMPs further demonstrate low toxicity in-vitro and in-vivo. Based on activity measures at 50% hemolysis ($HC_{50}$) and lethal dose 50% ($LD_{50}$), both peptides demonstrated biocompatibility, as both of their $HC_{50}$ and $LD_{50}$ values were much higher than their minimum inhibitory concentration values (MIC) values, (FK13, SEQ ID NO: 2, being more biocompatible than YI12, SEQ ID NO: 1. More importantly, the $LD_{50}$ values of both peptides compare favorably with that of polymyxin B (at 20.5 milligrams/kilogram (mg/kg)), which is a clinically used antimicrobial medication for treatment of antibiotic-resistant gram-negative bacterial infection.

The AI-designed peptides YI12 (SEQ ID NO: 1) and FK13 (SEQ ID NO: 2) were included in an initial set of about 100,000 candidate peptides generated using the CLaSS method. The initial set of 100,000 candidate peptides was reduced to 163 candidate peptides using a heuristic-based screening process that filtered the 100,000 candidate peptides using an independent set of binary (yes/no) sequence-level deep neural net-based classifiers that predict antimicrobial function, broad-spectrum efficacy, presence of secondary structure, and toxicity. The 163 candidate peptides were then simulated to test for membrane-binding tendency in accordance with a computer simulation screening process, which resulted in identification of 20 lead candidate peptides that exhibited high and consistent membrane-binding activity in the computer simulations. The 20 lead candidate peptides have the following sequences: YLRLIRYMAKMI (SEQ ID NO: 1), FPLTWLKWWKWKK (SEQ ID NO: 2), HILRMRIRQMMT (SEQ ID NO: 3), ILLHAILGVRKKL (SEQ ID NO: 4), YRAAMLRRQYMMT (SEQ ID NO: 5), HIRLMRIRQMMT (SEQ ID NO: 6), HIRAMRIRAQMMT (SEQ ID NO: 7), KTLAQLSAGVKRWH (SEQ ID NO: 8), HILRMRIRQGMMT (SEQ ID NO: 9), HRAIMLRIRQMMT (SEQ ID NO: 10), EYLIEVRESAKMTQ (SEQ ID NO: 11), GLITMLKVGLAKVQ (SEQ ID NO: 12), YQLLRIMRINIA (SEQ ID NO: 13), LIQVAPLGRLLKRR (SEQ ID NO: 14), LIQVAPLGRLLKRR (SEQ ID NO: 15), YQLRLIMKYAI (SEQ ID NO: 16), HRALMRIRQCMT (SEQ ID NO: 17), GWLPTEKWRKLC (SEQ ID NO: 18), YQLRLMRIMSRI (SEQ ID NO: 19), LRPAFKVSK (SEQ ID NO: 20).

The 20 lead candidate peptides were then synthesized and tested using wet laboratory experiments for antimicrobial activity and toxicity. Peptides YI12 (SEQ ID NO: 1) and FK13 (SEQ ID NO: 2) were identified from among the top 20 lead candidates based on their superior in-vitro antimicrobial activity. These two final lead AI-designed peptides among were further experimentally validated with strong broad-spectrum anti-microbial activity and low in vitro and in vivo toxicity. Both YI12 (SEQ ID NO: 1) and FK13 (SEQ ID NO: 2) were not present in the supervised training data used to design the initial CLaSS candidate peptides.

As used herein, the term "AI-designed molecule" is used to refer to a molecule that was designed, generated, or otherwise developed using one or more machine learning (ML) and/or AI techniques. The disclosed AI-designed molecules can include biological molecules (e.g., natural and recombinant peptides, proteins, biopolymers, nucleic acids, polysaccharides, antibodies, hormones, etc.), synthetic molecules, biopharmaceuticals (or "biologics"), and combinations thereof. The disclosed AI-designed molecules can include organic compounds, inorganic compounds, organometallic compounds, or combinations thereof.

The term "peptide" as used herein refers to a polymer of amino acid residues typically ranging in length from 2 to about 50 residues. In certain embodiments the AI-designed peptides disclosed herein range from about 2 to 25 residues in length. In some embodiments the amino acid residues comprising the peptide are "L-form" amino acid residues, however, it is recognized that in various embodiments, "D" amino acids can be incorporated into the peptide. Peptides also include amino acid polymers in which one or more amino acid residues is an artificial chemical analogue of a corresponding naturally occurring amino acid, as well as to naturally occurring amino acid polymers.

As used herein, the term "synthetic" peptide or synthetic AMP is used to refer to a peptide that is chemically synthesized as opposed to host derived. The term "residue" as used herein refers to natural, synthetic, or modified amino acids. Various amino acid analogues include, but are not limited to 2-aminoadipic acid, 3-aminoadipic acid, beta-alanine (beta-aminopropionic acid), 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic acid, 2,4 diaminobutyric acid, desmosine, 2,2'-diaminopimelic acid, 2,3-diaminopropionic acid, n-ethylglycine, n-ethylasparagine, hydroxylysine, allo-hydroxylysine, 3-hydroxyproline, 4-hydroxyproline, isodesmosine, allo-isoleucine, n-methylglycine, sarcosine, n-methylisoleucine, 6-n-methyllysine, n-methylvaline, norvaline, norleucine, ornithine, and the like. These modified amino acids are illustrative and not intended to be limiting.

The terms "conventional" and "natural" as applied to peptides herein refer to peptides, constructed only from the naturally-occurring amino acids: Ala, Cys, Asp, Glu, Glu, Phe, Gly, His, Ile, Lys, Leu, Met, Asn, Pro, Gln, Arg, Ser, Thr, Val, Trp, and Tyr. In various embodiments, the disclosed AI-designed peptides comprise only of natural amino acid residues. In some embodiments, the disclosed AI-designed molecules can substitute one or more synthetic or modified amino acids for a corresponding natural amino acid. A compound of the invention "corresponds" to a natural peptide if it elicits a biological activity (e.g., antimicrobial activity) related to the biological activity and/or specificity of the naturally occurring peptide. The elicited activity may be the same as, greater than or less than that of the natural peptide. In general, such a peptide will have an essentially corresponding monomer sequence, where a natural amino acid is replaced by an N-substituted glycine derivative, if the N-substituted glycine derivative resembles the original amino acid in hydrophilicity, hydrophobicity, polarity, etc. It should further be appreciated that the disclosed peptides can include the primary sequences disclosed herein, and conservatively modified variants thereof.

In certain embodiments, AMPs compromising at least 80%, preferably at least 85% or 90%, and more preferably at least 95% or 98% sequence identity with any of the sequences described herein are also contemplated. The terms "identical" or percent "identity," refer to two or more sequences that are the same or have a specified percentage of amino acid residues that are the same, when compared and aligned for maximum correspondence, as measured using one of the following sequence comparison algorithms or by visual inspection. With respect to the peptides disclosed herein sequence identity is determined over the full length of the peptide. For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted using a basic local alignment search tool (BLAST) or the like.

The term "specificity" when used with respect to the antimicrobial activity of a peptide indicates that the peptide preferentially inhibits growth and/or proliferation and/or exterminates a particular microbial species as compared to other related species. In certain embodiments the preferential inhibition or exterminate is at least 10% greater (e.g., the $LD_{50}$ being 10% lower), preferably at least 20%, 30%, 40%, or 50%, more preferably at least 2-fold, at least 5-fold, or at least 10-fold greater for the target species.

"Treating" or "treatment" of a condition as used herein may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

The term "high" as used with respect to antimicrobial activity and/or potency is used herein to indicate that the level of antimicrobial activity of an antimicrobial agent (e.g., an AMP or the like) is greater than a defined minimum threshold of antimicrobial activity or potency for a particular bacterial organism. In various embodiments, the minimum threshold can be based on its MIC, its $LD_{50}$ concentration/or its $HC_{50}$, concentration, wherein the lower the concentration, the higher the antimicrobial activity and/or potency. For example, in some embodiments, an antimicrobial agent can be considered to have high antimicrobial activity and/or potency if its MIC is less than 250 micrograms per milliliter (μg/mL), more preferably less than 150 μg/mL, more preferably less than 100 μg/mL, more preferably less than 50 μg/mL, and even more preferably less than 30 μg/mL.

The term "low-toxicity" is used herein to indicate any level of toxicity of a pharmacological agent (e.g., including one or more AMPs or another active agent) that is less than defined acceptable threshold of toxicity. In various embodiments, the defined threshold can be based on the MIC of the pharmacological agent relative to its $LD_{50}$ and/or $HC_{50}$ concentration. In some implementations, a pharmacological agent (e.g., an AMP or a composition comprising one or more AMPs) can be considered to have low-toxicity if its MIC is less than its $LD_{50}$ and/or $HC_{50}$ concentration. In other implementations, a pharmacological agent can be considered to have low-toxicity if its MIC is 60% or less than its $LD_{50}$ and/or $HC_{50}$ concentration. In other implementations, a pharmacological agent can be considered to have low-toxicity if its MIC is 50% or less than its $LD_{50}$ and/or $HC_{50}$ concentration. In other implementations, a pharmacological agent can be considered to have low-toxicity if its MIC is 30% or less than its $LD_{50}$ and/or $HC_{50}$ concentration. In other implementations, a pharmacological agent can be considered to have low-toxicity if its MIC is 25% or less than its $LD_{50}$ and/or $HC_{50}$ concentration.

One or more embodiments are now described with reference to the drawings, wherein like reference numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details. It is noted that the drawings of the present application are provided for illustrative purposes only and, as such, the drawings are not drawn to scale.

FIG. 1 provides a high-level flow diagram of an example computer-implemented method 100 for AMP design using deep generative models and controllable sampling, in accordance with one or more embodiments of the disclosed subject matter.

In various embodiments, elements described in connection with the disclosed computer-implemented method(s) can be embodied in different forms such as a computer system, a computer program product, or another form. One or more operations of method 100 can be performed by various types of computer systems comprising (or operatively coupled to) at least one process, and at least one memory, wherein the at least one memory stores executable instructions that, when executed by the processor, facilitate performance of described operations. In this regard, one or more of the operations described with reference to method 100 can be defined or otherwise embodied within one or more machine-executable components embodied within one or more machines (e.g., embodied in one or more computer readable storage mediums associated with one or more machines). Such components, when executed by the one or more machines (e.g., processors, computers, computing devices, virtual machines, etc.) can cause the one or more machines to perform the operations described. Examples of said processor and memory, as well as other suitable computer or computing-based elements, can be found with reference to FIG. 9 with respect to processing unit 916 and system memory 914, and can be used in connection with implementing one or more of the operations shown and described in connection with FIG. 1 or other figures disclosed herein.

In one or more embodiments, the disclosed AI-designed AMPs comprise peptides with amino acids sequences that were designed using method 100. Method 100 involves the synergistic use of deep generative neural networks for de novo design of new and minimalist peptides that are potent and nontoxic AMP candidates. In accordance with method 100, an informative latent space of peptides is learned using a probabilistic deep autoencoder in an unsupervised fashion, which enables attribute-conditioned sampling of novel antimicrobial candidates.

In this regard, at 102, method 100 comprises training, by a system operatively coupled to a processor, a peptide generative autoencoder model to reconstruct peptide sequences. At 104, method 100 comprises mapping, by the system, sparse peptide attributes to a low-dimensional latent space in association with the training. Operations 102 and 104 of method 100 collectively provide for generating a meaningful representation (in a latent space) of peptide sequences. The term "low-dimensional" with respect to the latent space is used herein to refer to dimensionality reduction with respect to the amount of features or variables included in the input sequences. In this regard, the "low-dimensional" latent space provides a representation the input sequences with fewer features or variables relative to the input sequences prior to encoding. At 106, method 100 comprises generating, by the system, AMPs using attribute-conditioned sampling from the low dimensional space, which is a process referred to as conditional latent (attribute) space sampling or CLaSS.

Figure 2A:
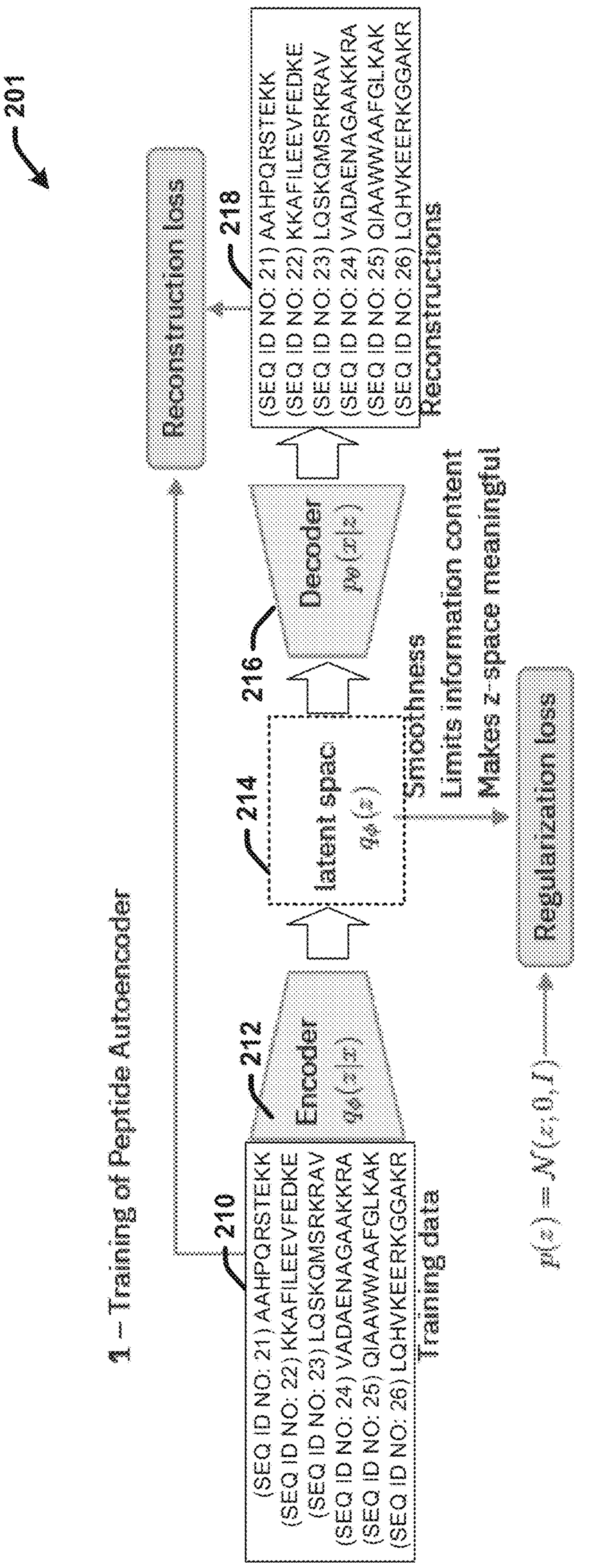
FIGS. 2A-2C provide detailed flow-diagrams for the respective training, mapping and sampling operations of the disclosed AMP design techniques in accordance with one or more embodiments of the disclosed subject matter.
Figure 2B:
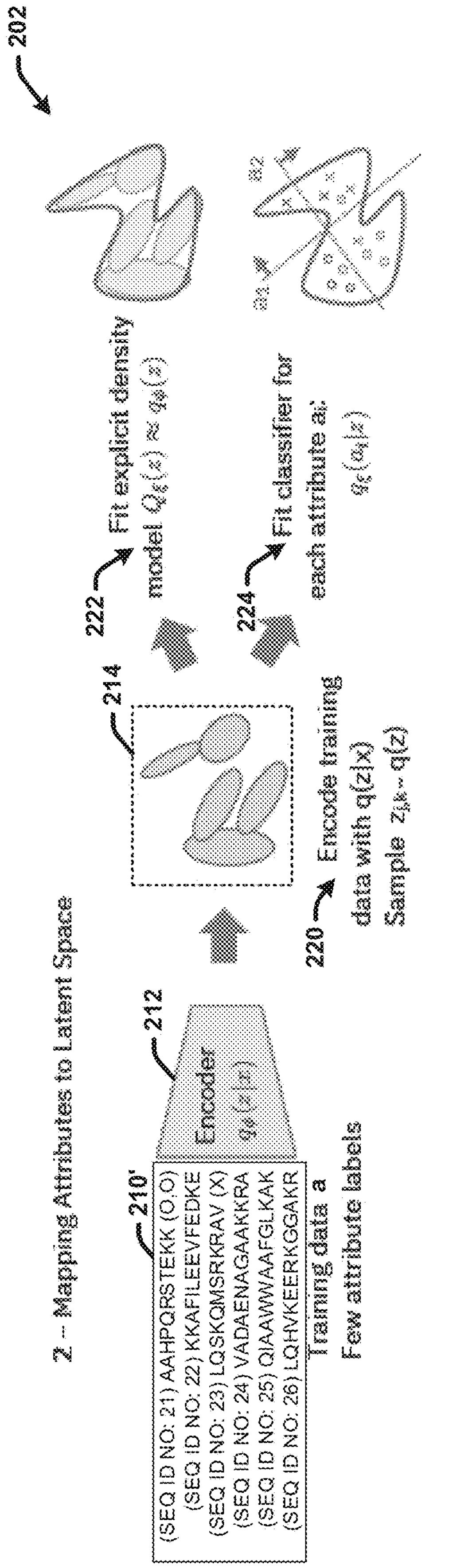
Figure 2C:
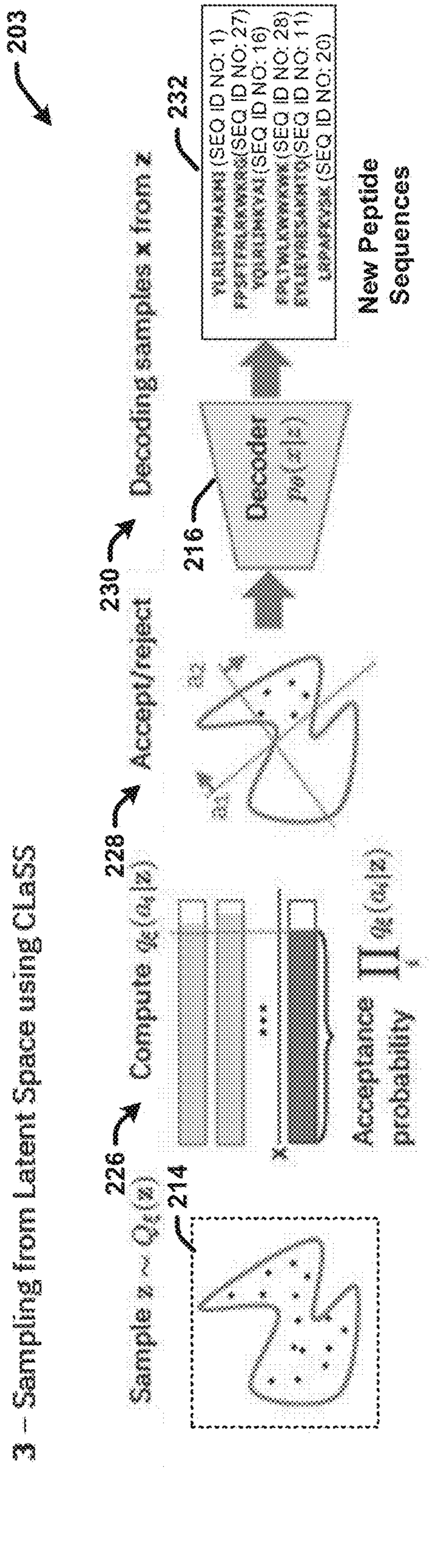

FIGS. 2A-2C provide detailed flow-diagrams for the respective training, mapping and sampling operations of method 100 in accordance with one or more embodiments.

With reference initially to FIG. 2A, presented is an example computer-implemented process 201 for training the peptide autoencoder. In particular, the peptide generative autoencoder model can include a deep autoencoder model than consists of an encoder neural network (encoder 212) and a decoder neural network (decoder 216). Such autoencoder models generally work by mapping input data into a latent representation in feature space (e.g., latent space 214) which is then decoded by the decoder network to generate a desired output. As applied to the de novo design of AMPs, the encoder 212 can be trained to encode peptide sequences included in training data 210 into latent variables that are mapped to a latent space 214. Likewise, the decoder 216 can be trained to decode (reconstruct) the data from latent variables. For example, the decoder 216 can be trained to decode or reconstruct the same input sequences based on the latent variables as included in the latent space 214, resulting in the reconstructions 218. In this regard, the reconstructions 218 should be the same peptide sequences as the input sequences included in the training data 210.

In some embodiments, the peptide generative autoencoder can comprise a variational autoencoder (VAE). In other embodiments, the peptide generative autoencoder can comprise a Wasserstein Autoencoder (WAE). Other suitable autoencoders can also be used.

In this regard, as expressed mathematically, the encoder $q_\theta(z|x$: parameterized with $\phi$ can be trained to map the input x to a variational distribution, wherein x represents the input amino acid sequence, and z represents the latent variable. The decoder $p_\theta(x|z)$ parameterized with $\theta$ (wherein $\theta$ represents the learned parameters) aims to reconstruct the input x given the latent vector z from the learned distribution, as illustrated in accordance with process 201. A VAE assumes the latent variable $z \sim p(z)$ follows a simple prior (e.g., Gaussian) distribution and the decoder then produces a distribution over sequences given the continuous representation z. Thus, the generative process is specified by Equation 1 below, where the latent variable is integrated out.

$$p(x)=\int p(z)p_\theta(x|z)dz \qquad \text{Equation 1.}$$

However, a VAE that aims to minimize Kullback-Leibler (KL) distance between the encoded training distribution and prior reportedly suffers from ignoring the latent z-information during decoding. To address this issue, WAEs have been proposed, which are designed to minimize the optimal transport distance or Wasserstein distance. Within this VAE/WAE framework, the peptide generation by the decoder 216 can be formulated as a density modeling problem that involves estimating p(x) where x are short variable length strings of amino acids. The density estimation procedure has to assign high likelihood to known peptides. Therefore, the model generalization implies that plausible novel peptides can be generated from regions with a high probability density under the model.

In one or more embodiments, the input peptide training sequences in the training data 210 can be restricted to sequences comprising one or more desired attributes. For example, the one or more input peptide sequences can be restricted to sequences with less than or equal to 25 natural amino acid residues, or more preferably less than or equal to 20 (as shorter AMPs are preferable for synthesis cost reduction and peptide stability). In some embodiments, the autoencoder (i.e., the encoder and the decoder networks thereof) can be trained on known AMP sequences.

Additionally, or alternatively, the autoencoder can be trained using as least some unlabeled peptide sequences (e.g., wherein the antimicrobial (AMR) status is unknown). For example, in some embodiments, the autoencoder can trained using a large database of protein/peptide sequences that may or may not have annotation and limit selection of the training sequences to sequences that have a sequence length of N or less (e.g., 25 or less, 20 or less, etc.). For example, one suitable database known as UniProt can be used which has about 1.7 million peptide/protein sequences, and about 9000 annotated AMPs with a sequence length of 50 residues or less. When the autoencoder is trained on such a large corpus of training data including labeled and unlabeled AMPs, the resulting latent space 214 is expected to carry more information than learning solely from known AMP sequences, better capture the vast space of biological sequences, and add exploratory capability beyond known antimicrobial templates.

The autoencoder training results in the generation of latent space 214 generally referred to herein as the latent z-space or simply z-space. This z-space provides reduced dimensionality representation of encoded attributes from the training peptide sequences. With the end-goal of conditional generation of novel peptide sequences, it is crucial to ensure that the learned encoding in the z-space retains identifiable information about functional attributes of the original sequences. Based on some experimental evidence, the WAE autoencoder was found to provide the best results. In particular, an investigative study was performed to determine whether the evolutionary relationships between sequences are captured by their encodings in the latent z-space, as the evolutionary information is known to specify the biological function and fold of peptide sequences. The WAE model demonstrated a negative correlation between pairwise evolutionary similarities and z-space computed using k nearest neighbor calculations. Therefore, the WAE model was found to intrinsically capture the evolutionary relationship within the peptide space.

In addition, the latent z-space of the WAE model trained on known and unknown (i.e., unlabeled) AMPs was found to be linearly separable into different attributes using prediction classifiers, such that sampling from a specific region of that space yields consistent and controlled generations. The attributes represented in the latent z-space evaluated included antimicrobial activity, toxicity, evolutionary distance, as well as physiochemical properties including aromaticity, charge, and hydrophobic moment (indicating amphiphilicity of a helix) change smoothly during the interpolation. The results are encouraging, as the WAE latent space trained on the much larger amount of unlabeled data appears to carry significant structure in terms of functional, physicochemical, and evolutionary aspects. However, evaluation of the latent z-space of the WAE model found that some attributes such as toxicity are more challenging to detect than antimicrobial activity from the learned latent peptide representation and will be investigated in future. Thus, in various embodiments, the peptide autoencoder used can comprise a WAE model trained on labeled and unlabeled data.

With reference now to FIG. 2B, presented is an example mapping process 202 for mapping peptide attributes to the models latent z-space (operation 102 in method 100).

CLaSS leverages attribute classifiers directly trained on the peptide z-space (latent space 214), as those can capture important attribute information. The mapping process 202 demonstrates training of these attribute classifiers using the labeled sequences included in the training data, referred to in FIG. 2B as training data 210'.

In this regard, as expressed mathematically, the mapping process 202 formalizes that there are n different (and possibly independent) binary attributes of interest $a \in \{0,1\}^n = [a_1, a_2, \ldots, a_n]$, wherein each attribute a is only available (labeled) for a small and possibly disjoint subset of the dataset. Since functional annotation of peptide sequences is expensive and time consuming, current databases typically represent a small (e.g., about 10 to about 10,000) subset of the unlabeled corpus. We posit that all plausible datapoints have those attributes, albeit mostly without label annotation, therefore the data distribution implicitly is generated as $p(x) = \mathbb{E}_{a \sim p(a)}[p(x|a)]$, where the distribution over the (potentially huge) discrete set of attribute combinations p(a) is integrated out, and for each attribute combination the set of possible sequences is specified as p(x|a).

In this regard, at 220 the training data sequences are encoded by the encoder 212 during autoencoder training. At 222, the explicit density model is fit to learn over all known peptide sequences in the latent space. At 224, a classifier is fit for each attributed based on latent space variable encoded. At 224, a classifier is fit for each attributed based on latent space variable encoded.

FIG. 2C presents an example process 203 for generating new peptide sequences 232 using CLaSS by sampling from the latent space 214 in accordance with one or more embodiments. Once the attributes have been mapped to the latent space 214, the goal now is to sample conditionally $p(x|a_t)$ for a specified target attribute or target attribute combination $a_t$. This task can be approached through CLaSS, which makes the assumption that attribute conditional density factors as follows Equation 2:

$$p(x|a_t) = \mathbb{E}_z[p(z|a_t)p(x|z)] \quad \text{Equation 2.}$$

In this regard, $p(x|a_t)$ can be sampled approximately using rejection sampling from the models in the latent z-space $p(x|a_t)$ using rejection sampling from models in the latent z-space appealing to Bayes rule and $p(a_t|z)$, that is each attribute combination from the set of possible sequences as modeled by the attribute classifiers. In particular, the CLaSS method employs a trained classifier to sample from the latent-z space conditionally for a specified target attribute or target attribute combination. In this regard, the specific target attribute or target attribute combinations are sampled from the peptide-z space and then passed through the trained decoder network to generate new peptide sequences. The specific attribute and/or attribute combinations sampled can vary depending on the goal of the target peptide For example, in accordance with process 203, at 226, the classifiers are used to compute probabilities on each attribute. At 228, the system then determines whether to accept or reject the explicit density using an acceptance probability that is equal to the product of the classifiers' score. At 230, the decoder then decodes samples x from z to generate the new peptide sequences 232.

In one or more exemplary embodiments, a single binary classifier trained on the latent features for antimicrobial function (yes/no) was used as the sole condition for the CLaSS sampling from the peptide latent space of a WAE model trained on 100,000 unlabeled peptide sequences (whose AMR status was unknown) and about 5,000 known AMPs. Using this sole sampling condition from the peptide latent space, a set of about 90,000 candidate AMP sequences were generated.

To check the novelty of the set of CLaSS-generated AMP sequences, a BLAST sequence similarity (or homology) search was performed against the training dataset. The Expect value (E-value) returned by the BLAST indicates statistical (aka. biological) significance of the match between the query and database sequences. The E-value is a measure of the probability of the high similarity score occurring by chance when searching a database of a particular size. E-values decrease exponentially as the score of the match increases. Larger E-values indicate a greater chance that the similarity between the hit and the query is merely coincidence, (i.e. the match is less significant). Typically, E-values of about 0.001 when querying a Uniprot database of a size of about 220 million are used to infer homology. Since the training dataset used to generate the 90,000 candidate sequences was about 1000 times smaller than the Uniprot database, an E-value of about 1.0 or less provides a reasonable indication of non-homology. That is, if the closest hit for a query in the training database has an E-value of 1.0 or less, the query can be considered non-homologous or novel with respect to training sequences.

The BLAST resulted in about 14% of the generated sequences having an showed an E-value of 10 or greater, and another 36% having an E-value greater than 1.0, when considering only the match with highest alignment score, indicating insignificant similarity to training sequences. If the alignments with scores greater than 20 are only considered, the average E-value is still found to be about 2.0, implying the non-homologous nature of generated sequences with respect to the training sequences. The CLaSS-generated AMP are also diverse, as the unique (i.e. found only once in the database) k-mers (k=3-6) are more abundant compared to training sequences. These results highlight the ability of the present approach to generate minimalist AMP sequences that are on average highly novel with respect to training data as well as diverse among themselves.

Distributions of key molecular features implicated in antimicrobial nature, such as amino acid composition, charge, hydrophobicity (H), and hydrophobic moment (PH), were also compared between the training AMPs and the CLaSS generated AMPs. Based on this comparison, the CLaSS-generated AMP sequences show distinct character. Specifically, the CLaSS-generated AMPs are richer in R, L, S, Q and C residues, whereas A, G, D, H, N, and W content is reduced, in comparison to training antimicrobial sequences.

In addition, the most frequent 3 and 4 k-mers are K and L-rich in both the CLaSS generated and training AMPs, though the CLaSS generated sequences have much stronger tendency toward the prevalent k-mers. The CLaSS generated AMPs are also characterized by global charge and aromaticity somewhere in between the unlabeled and AMP-labeled training sequences, while their hydrophobic moments are comparable to that of known AMPs, indicating the generated AMPs are still cationic and can form putative amphiphilic $\alpha$-helix structures, similar to the majority of known antimicrobials. The CLaSS generated AMPs also exhibit moderately higher hydrophobic ratio and aliphatic index. These observations highlight the distinct physicochemical nature of the CLaSS-generated AMP sequences, which is a result of the semi-supervised nature of the autoencoder learning paradigm and may affect additional attributes (not explicitly included in the learning process). For example, lower aromaticity and higher aliphatic index are known to induce better oxidation susceptibility and higher heat stability in short peptides, while lower hydrophobicity is associated with reduced toxicity. As a result, AMP-conditioned CLaSS from WAE latent space has potential to produce novel antimicrobials that are better optimized in terms of stability and/or toxicity, when compared to training sequences.

CLaSS also has additional advantages regarding repurposability, as one can (1) learn the effective imposition of the functional/structural/physicochemical attributes post-hoc on the latent space, therefore does require minimal autoencoder retraining; and (2) perform controlled generation in a dynamic manner where attribute controls can be added or removed as desired. Unsupervised learning of the latent space using deep probabilistic autoencoders further enables candidate generation that are biologically meaningful, novel and optimal. The fundamental approach is similarly applicable to broader classes of material and molecule discovery challenges, which share aspects of the underlying data structure and attributes.

Figure 3:
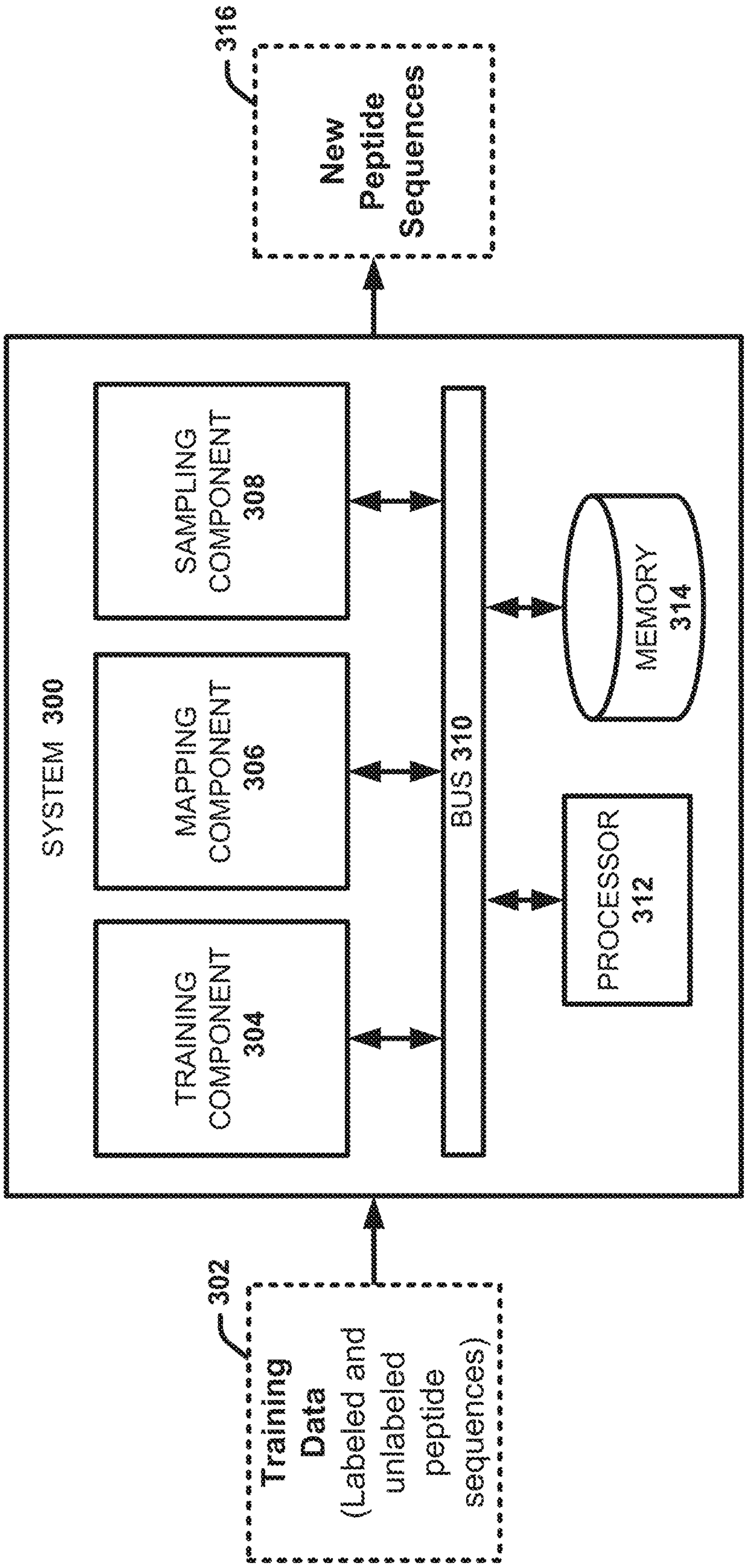
FIG. 3 presents a block diagram of an example, non-limiting system that facilitates AMP design using deep generative models and controllable sampling, in accordance with one or more embodiments of the disclosed subject matter.

FIG. 3 presents a block diagram of an example, non-limiting system 300 that facilitates AMP design using deep generative models and controllable sampling, in accordance with one or more embodiments of the disclosed subject matter. Embodiments of systems described herein can include one or more machine-executable components embodied within one or more machines (e.g., embodied in one or more computer readable storage mediums associated with one or more machines). Such components, when executed by the one or more machines (e.g., processors, computers, computing devices, virtual machines, etc.) can cause the one or more machines to perform the operations described.

System 300 provides computer-executable components that can perform the various operations described with reference to FIGS. 1, 2A, 2B and 2C. For example, system 300 can include training component 304, mapping component 306 and sampling component 308.

With reference to FIGS. 1 and 2A, in one or more embodiments, the autoencoder training described with reference to 102 and process 201 can be performed by the training component 304 using training data 302. In this regard, the training data 302 can include at unlabeled peptide sequences and least some labeled peptide sequences that are labeled with feature information identifying one or more features of the respective peptides, including but not limited to: evolutionary distance parameters, functional attributes (e.g., including AMP status, toxic class probabilities, etc.), and physicochemical properties (e.g., aromaticity, charge, hydrophobic moment that indicates amphiphilicity of a helix, and the like. In addition, the mapping operations described with reference to 104 and process 202 can be performed by the mapping component 306. Further, the CLaSS operations described with reference to 106 and process 203 can be performed by the sampling component 308 to generate new peptide sequences 316 as AMR candidates. For example, in one or more implementations, the new peptide sequences 316 can include or correspond to the set of about 90,000 CLaSS generated peptide sequence candidates described above and/or the new peptide sequences 232. Repetitive description of like elements employed in respective embodiments is omitted for sake of brevity.

System 300 can further include or be operatively coupled to at least one memory 314 and at least one processor 312. In various embodiments, the at least one memory 314 can store executable instructions (e.g., the training component 304, the mapping component 306 and the sampling component 308) that when executed by the at least one processor 312, facilitate performance of operations defined by the executable instructions. System 300 can further include a device bus 310 that communicatively couples the various components of the system 300. Examples of said processor 312 and memory 314, as well as other suitable computer or computing-based elements, can be found with reference to FIG. 11 with respect to processing unit 1116 and system memory 1114, and can be used in connection with implementing one or more of the systems or components shown and described in connection with FIG. 3 or other figures disclosed herein.

In some embodiments, system 300 can be deployed using any type of component, machine, device, facility, apparatus, and/or instrument that comprises a processor and/or can be capable of effective and/or operative communication with a wired and/or wireless network. All such embodiments are envisioned. For example, system 200 can be deployed by, run by, and/or otherwise executed by a server device, a computing device, a general-purpose computer, a special-purpose computer, a tablet computing device, a handheld device, a server class computing machine and/or database, a laptop computer, a notebook computer, a desktop computer, a cellular phone, a smart phone, a consumer appliance and/or instrumentation, an industrial and/or commercial device, a digital assistant, a multimedia Internet enabled phone, a multimedia player, and/or another type of device.

It should be appreciated that the embodiments of the subject disclosure depicted in various figures disclosed herein are for illustration only, and as such, the architecture of such embodiments are not limited to the systems, devices, and/or components depicted therein. In some embodiments, one or more of the components of system 300 can be executed by different computing devices (e.g., including virtual machines) separately or in parallel in accordance with a distributed computing system architecture. System 300 can also comprise various additional computer and/or computing-based elements described herein with reference to operating environment 1100 and FIG. 11. In several embodiments, such computer and/or computing-based elements can be used in connection with implementing one or more of the systems, devices, components, and/or computer-implemented operations shown and described in connection with FIG. 3 or other figures disclosed herein.

The disclosed subject matter further provides novel AI-designed AMPs that were included in the set of about 90,000 CLaSS generated peptide sequence candidates described above using additional screening and wet-laboratory testing. These novel AMPs include one with twelve, natural amino acids in length and the amino acid sequence YLRLIRYMAKMI (SEQ ID NO: 1), referred to herein as YI12; and another with thirteen, natural amino acids in length and the amino acid sequence FPLTWLKWWKWKK (SEQ ID NO: 2), referred to herein as FK13.

To screen the initial set of about 90,000 CLaSS-generated AMP sequences for experimental validation, an independent set of four binary (yes/no) sequence-level deep neural net-based classifiers were used to predict antimicrobial function, broad-spectrum efficacy (e.g., activity on both Gram positive and Gram negative strains), presence of secondary structure, as well as toxicity, in accordance with a heuristics-based screening process. In particular, a bidirectional LSTM-based classifier was trained for each of the four attributes on a labeled training dataset for known peptide sequences with a hidden layer size of 100 and a dropout of 0.3. Based on the distribution of the scores (classification probabilities/logits), the threshold was determined by considering the $50^{th}$ percentile (median) of the scores. The screening criteria used to select the first subset of candidates from the initial 90,000 viable candidates thus considered all four attributes. The initial set of 90,000 candidate peptides was reduced to 163 candidate peptides using this heuristic-based screening process.

The 163 candidate peptides were then subjected to coarse-grained Molecular Dynamics (CGMD) simulations of peptide-membrane interactions to test for membrane-binding tendency in accordance with a physics-based simulation screening process. In particular, the molecular simulation process involves using high-throughput computer simulations to simulate the molecular interactions between respective candidates included the filtered subset and one or more molecular and/or biological targets (e.g., one or more cellular components of a pathogen). The simulated molecular interactions can be used to identify one or more of the candidates that exhibit one or more behavioral characteristics of interest (i.e., target characteristics). As applied to screen the 163 candidate CLaSS generated AMPs, the high-throughput computer simulations were used to evaluate the candidate peptides for consistent interaction propensity with a modeled lipid bilayer.

Figure 4:
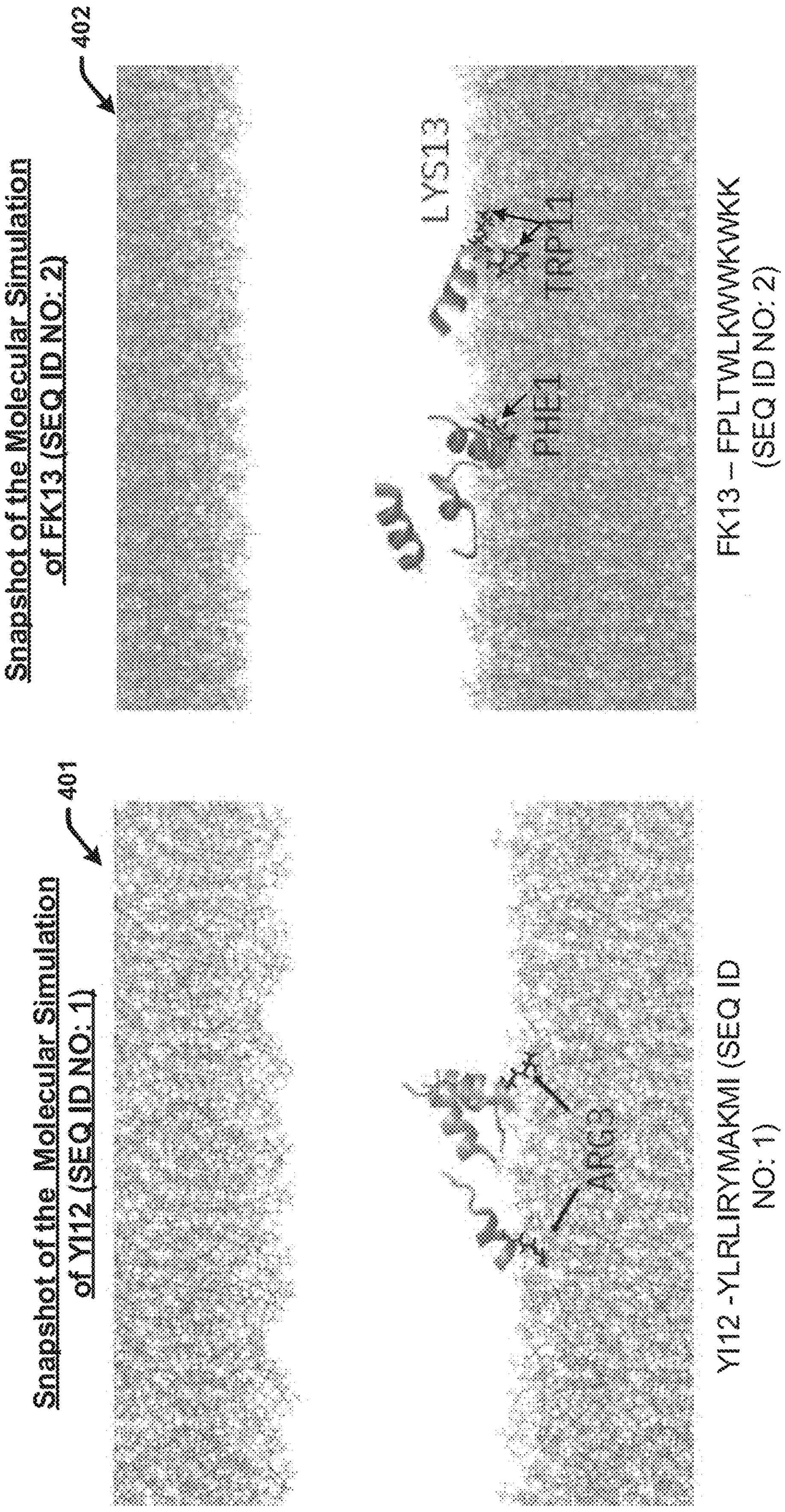
FIG. 4 provides snapshot images of the molecular simulations performed for AMPs YI12 (SEQ ID NO: 1) and FK13 (SEQ ID NO: 2) in accordance with one or more embodiments.

For example, FIG. 4 provides snapshot images of the molecular simulations performed for AMPs YI12 (SEQ ID NO: 1) and FK13 (SEQ ID NO: 2) in accordance with one or more embodiments. Image 401 provides a snapshot of the molecular simulation performed for YI12 (SEQ ID NO: 1) and image 402 provides a snapshot of the molecular simulation performed for FK13 (SEQ ID NO: 2). To conduct these molecular simulations, the candidate peptides were modeled with an all-atom representation of the peptide given its protein sequence (e.g., which in this case were both alpha helixes). The model lipid bilayer was modelled using a forcefield model (e.g., a coarse-grained forcefield model or the like). The modeled peptide structures were further transformed into course-grained representations and combined with the membrane model to create a course-grained peptide-membrane system for simulation.

In accordance with these simulations, the respective candidate peptides were interacted with the membrane for 1.0 microsecond (μs). The membrane interaction propensity was then evaluated based the number of contacts/touch points between the peptide and the membrane and the stability of those contacts. Selected residues of the respective modelled peptides that interact with the membrane are highlighted in the images.

In this regard, antimicrobial propensity was found to strongly correlate with the number of contacts and the contact stability, wherein the greater the number of contacts and the greater stability of those contacts, the greater probability of antimicrobial propensity. The contacts can include contacts between the positive residues of the peptide and the membrane. In one or more implementations, the number of contacts between positive residues and the lipid membranes is defined as the number of atoms belonging to a lipid at a distance less than 7.5 Å from a positive residue of the peptide. Contact stability was measured as a function of the variance in the number of contacts, wherein the lower the variance the greater the stability and thus the higher indication of strong antimicrobial activity. Specifically, the contact variance distinguishes between high potency and non-antimicrobial sequences with a sensitivity of 88% and a specificity of 63%. Physically, this feature can be interpreted as measuring the robust binding tendency of a sequence to model membrane. Therefore, a contact variance cutoff of 2.0 was used for screening the 163 AMP sequences.

The simulation-based screening resulted in identification of 20 lead candidate peptides that exhibited high and consistent membrane-binding activity in the computer simulations. The 20 lead candidate peptides have the following sequences: YLRLIRYMAKMI (SEQ ID NO: 1), FPLTWLKWWKWKK (SEQ ID NO: 2), HILRMRIRQMMT (SEQ ID NO: 3), ILLHAILGVRKKL (SEQ ID NO: 4), YRAAMLRRQYMMT (SEQ ID NO: 5), HIRLMRIRQMMT (SEQ ID NO: 6), HIRAMRIRAQMMT (SEQ ID NO: 7), KTLAQLSAGVKRWH (SEQ ID NO: 8), HILRMRIRQGMMT (SEQ ID NO: 9), HRAIMLRIRQMMT (SEQ ID NO: 10), EYLIEVRESAKMTQ (SEQ ID NO: 11), GLITMLKVGLAKVQ (SEQ ID NO: 12), YQLLRIMRINIA (SEQ ID NO: 13), LIQVAPLGRLLKRR (SEQ ID NO: 14), LIQVAPLGRLLKRR (SEQ ID NO: 15), YQLRLIMKYAI (SEQ ID NO: 16), HRALMRIRQCMT (SEQ ID NO: 17), GWLPTEKWRKLC (SEQ ID NO: 18), YQLRLMRIMSRI (SEQ ID NO: 19), LRPAFKVSK (SEQ ID NO: 20). Based on the CLaSS design method, the heuristics based screening process and the results of the molecular simulations, all of these peptide sequences (and conservatively modified variants thereof), demonstrate or are otherwise attributed to having several important antimicrobial characteristics, including but not limited to: antimicrobial activity, broad-spectrum antimicrobial activity, a secondary structure (e.g., an alpha helix or coil), low toxicity, and consistent membrane-binding activity. In addition, these top 20 CLaSS generated AMPs are novel peptides, as demonstrated based on the BLAST results described above.

These 20 lead candidate peptides were then synthesized and tested using wet laboratory experiments for antimicrobial activity and toxicity. All of the 20 candidate peptides were synthesized and tested with a terminal amide group (—CONH2) appended thereto. In this regard, all of the peptides were amidated at their C-terminus to remove the negative charge of the C-terminal carboxyl group. The broth microdilution method was used to measure MIC values of the candidate AMPs against Gram-positive *S. aureus* and Gram-negative *E. coli*. Among these 20 lead peptides, the two AMPs YI12 (SEQ ID NO: 1) and FK13 (SEQ ID NO: 2) were identified to be the best with the lowest MIC values. These two novel AMPs were further experimentally validated using wet-laboratory experiments and demonstrated strong broad-spectrum anti-microbial activity and low in vitro and in vivo toxicity. Both of YI12 (SEQ ID NO: 1) and FK13 (SEQ ID NO: 2) were not present in the supervised training data used to design the initial candidate CLaSS peptides. These experiments and results are now described in greater detail with reference to FIGS. 5-9B.

FIG. 5 presents a table (Table 500) presenting minimum inhibitory concentrations (MICs) determined for the 20 AI-designed AMP candidate sequences against Gram-positive *S. aureus* and Gram-negative *E. coli*. Among the 20 AI-designed AMP candidates, two sequences, YLRLIRYMAKMI-CONH2 (referred to a YI12 (SEQ ID NO: 1) with 12 amino acids) and FPLTWLKWWKWKK-CONH2 (referred to a FK13 (SEQ ID NO: 2) with 13 amino acids), were identified to be the best with the lowest MIC values. These two sequences are highlighted in Table 300. Both peptides (YI12 (SEQ ID NO: 1) and FK13 (SEQ ID NO: 2)) were positively charged and have a nonzero hydrophobic moment, indicating their cationic amphiphilic nature in line with known antimicrobials.

In addition to the 20 AI-designed AMP candidate sequences, 11 generated non-AMP sequences were also screened for antimicrobial activity that was measured by MIC, lower the better against Gram-positive *S. aureus* and Gram-negative *E. coli*. None of the designed non-AMP sequences showed MIC values that are low enough to be considered as antimicrobials, implying that our approach does not tend to yield false negative predictions.

Peptides YI12 (SEQ ID NO: 1) and FK13 (SEQ ID NO: 2) were further evaluated against more difficult-to-treat Gram negative *P. aeruginosa* and *A. baummannii*, as well as a multi-medication-resistant (MDR) Gram negative *K. pnuemoniae*, as shown in FIG. 6.

In this regard, FIG. 6 provides a table (Table 400) illustrating the broad-spectrum antimicrobial activity (measured in MIC) and toxicity of YI12 (SEQ ID NO: 1) and FK13 (SEQ ID NO: 2). As shown in Table 400 both YI12 (SEQ ID NO: 1) and FK13 (SEQ ID NO: 2) showed potent broad-spectrum antimicrobial activity with comparable MIC values against all five evaluated bacterial strains.

Figure 7:
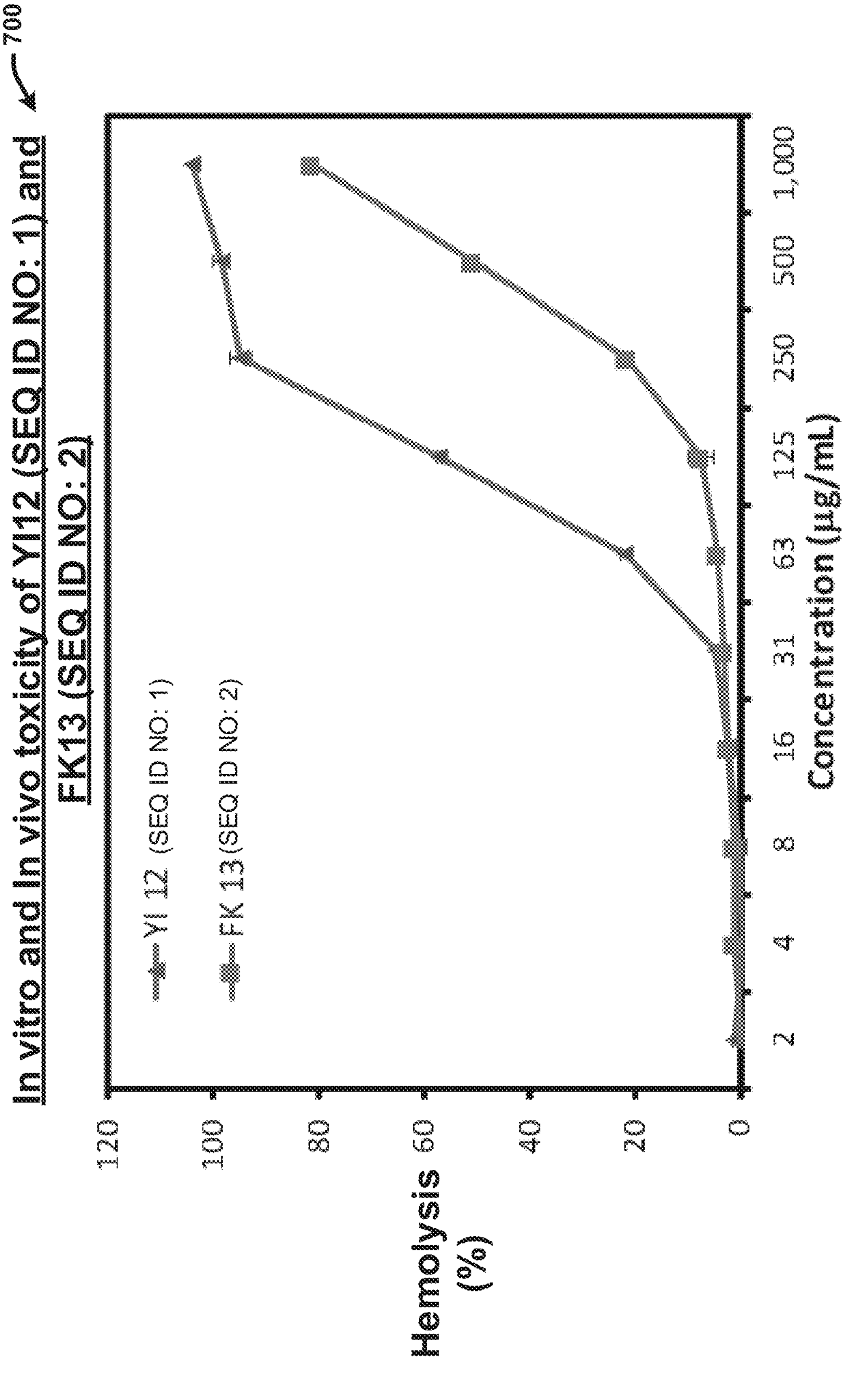
FIG. 7 provides a graph illustrating the in-vitro and in-vivo toxicity of YI12 and FK13.

In vitro and in vivo testing for selectivity (hemolytic activity) and toxicity was also performed, the results of which are shown in Table 600 and Graph 700 of FIG. 7. FIG. 7 provides a graph 700 illustrating the in-vitro and in-vivo selectivity/toxicity of YI12 (SEQ ID NO: 1) and FK13 (SEQ ID NO: 2).

In this regard, the selectivity of two novel AMPs towards bacteria over mammalian cells was studied using rat red blood cells (rRBCs), which were obtained from Animal Handling Unit of Biomedical Research Center, Singapore 1. Untreated rRBC suspension in phosphate buffered saline were uses as a negative control, and rRBC suspension treated with 0.1% Triton X were uses as a positive control. The percentage of hemolysis of rRBCs was obtained using the following formula:

$$\text{Hemoloysis (\%)} = \frac{O.D._{576mm} of treated samples - O.D._{576mm} of negative control}{O.D._{576mm} of positive sample - O.D._{576mm} of negative control}. \qquad \text{Formula 1}$$

For acute in vivo toxicity, the animal study protocols were approved by the Institutional Animal Care and Use Committee of Biological Resource Center, Agency for Science, technology and Research Singapore. The $LD_{50}$ values of the AMPs, dose required to exterminate 50% mice, were determined using a previously reported protocol. Specifically, Balb/c mice (8 weeks old, 18-22 g) were employed. Both of the AMPs were separately dissolved in saline and administered to mice by intraperitoneal (i.p) injection at various doses. Mortality was monitored for 14 days post AMP administration, and the $LD_{50}$ values were estimated using the maximum likelihood method.

With reference to FIG. 6 and Table 600 based on activity measure at 50% hemolysis ($HC_{50}$) and $LD_{50}$ values, both peptides demonstrate biocompatibility, as both of their $HC_{50}$ and $LD_{50}$ values are much higher than their MIC values, with FK13 (SEQ ID NO: 2) being more biocompatible than YI12 (SEQ ID NO: 1). More importantly, the $LD_{50}$ values of both peptides compare favorably with that of polymyxin B (at 20.5 mg/kg), which is a commonly used clinical antimicrobial medication for treatment of antibiotic-resistant Gram-negative bacterial infections in humans and other mammals.

These results show that CLaSS designed peptides using a peptide latent space modeled by a WAE model can generate AMP design leads with both efficacy and selectivity at a success rate of 10%. In addition, the whole cycle, from database curation to wet lab confirmation, takes 48 days in total and a single iteration, thereby significantly decreasing the timeline and costs for novel medication discovery. For example, currently, the minimum cost to synthesize and test a single AMP candidate in the wet laboratory environment is between three to five thousand dollars. In addition, the average time to synthesize and test even only 20 candidates in the wet lab is about a month. Accordingly, the development of new pharmaceuticals and other novel molecules using ML and AI is significantly hindered by this highly expensive and time-consuming pipeline. Thus, the disclosed CLaSS molecular design techniques, combined with the downstream heuristic-based and molecular simulation screening process, provide substantial improvements in the field of medication design and discovery.

FIGS. 8A and 8B presents the basic local alignment search tool (BLAST) search results of YI12 (SEQ ID NO: 1) and FK13 (SEQ ID NO: 2), respectively. In particular, the novelty of YI12 (SEQ ID NO: 1) and FK13 (SEQ ID NO: 2) with respect was further evaluated using similarity metrics generated using the BLAST homology search tool. These similarity metrics include alignment scores, E-values, percentage of alignment coverages, percentage of identity, percentage of positive matches or similarity, and percentage of alignment gap.

Both YI12 (SEQ ID NO: 1) and FK13 (SEQ ID NO: 2) were searched using BLAST against the training sequences (about 180,000) used to train the WAE model and CLaSS conditional classifiers used to generate the CLaSS designed candidate peptides included in the initial set of about 90,000 peptides. BLAST searching with an E-value threshold of 10 against the training database did not reveal any match for YI12 (SEQ ID NO: 1), suggesting that there exists no statistically significant match to YI12 (SEQ ID NO: 1). Therefore, related sequences of YI12 (SEQ ID NO: 1) were further searched in the much larger Uniprot database consisting of about 223.5 million non-redundant sequences, wherein only a fraction of which was included in the WAE model training. FIG. 8A presents the BLAST search results of YI12 (SEQ ID NO: 1) against 223.5 million Uniprot sequences, and FIG. 8B presents the BLAST search results of FK13 (SEQ ID NO: 2) against 180,000 training sequences.

As shown in FIG. 8A, the closest match to YI12 (SEQ ID NO: 1) shows an E-value of 2.9 with 75% identity, 83% similarity, a gap of 1.0 at a query coverage of 92%, which is an 11-residue segment from the bacterial EAL domain-containing protein. This result suggests that YI12 (SEQ ID NO: 1) is significantly high in novelty, even when all protein sequences in Uniprot are considered. A BLAST search of YI12 (SEQ ID NO: 1) against the PATSEQ database containing 65.5 million patented peptides was also searched and still received a minimum E-value of 1.66. The sequence nearest to YI12 (SEQ ID NO: 1) from PATSEQ is an 8 amino acid long segment from a 79 amino acid long human protein, which has with 87.5% similarity and only 66.7% coverage, further confirming YI12's (SEQ ID NO: 1) high degree of novelty.

As shown in FIG. 8B, FK13 shows less than 75% identity as well as a gap in the alignment (indicating presence of additional amino acids) with an 85% query coverage to its closest match in training database, demonstrating that FK13 is also novel. The closest match of FK13 in the training database is a synthetic variant of a 13 amino acid long bactericidal domain (PuroA: FPVTWRWWKWWKG) of a Puroindoline-A protein from wheat endosperm. The antimicrobial and hemolysis activities of FK13 are similar to those reported for PuroA (57,58). Nevertheless, FK13 is significantly different from PuroA; FK13 is K-rich and low in W-content, resulting in a lower Grand Average of Hydropathy (GRAVY) score (−0:854 vs. −0:962), a higher aliphatic index (60:0 vs. 22:3), and a lower instability index (15:45 vs. 58:30), all together indicative of higher peptide stability. In fact, lower W-content was beneficial for stability of FK13 during wet lab experiments, since Tryptophan (W) is susceptible to oxidation in air. Lower W-content has also been implicated in improved in-vivo peptide stability. Rational design and optimization of existing AMPs toward additional properties (e.g. stability) while retaining their antimicrobial activity and low toxicity is a challenging task. In fact, there exists a naturally occurring sequence (PuroB: FPVTWPTKWWKG) that is remarkably similar to PuroA but exhibits no significant antimicrobial activity (MIC>200 µg/ml).

Figure 9A:
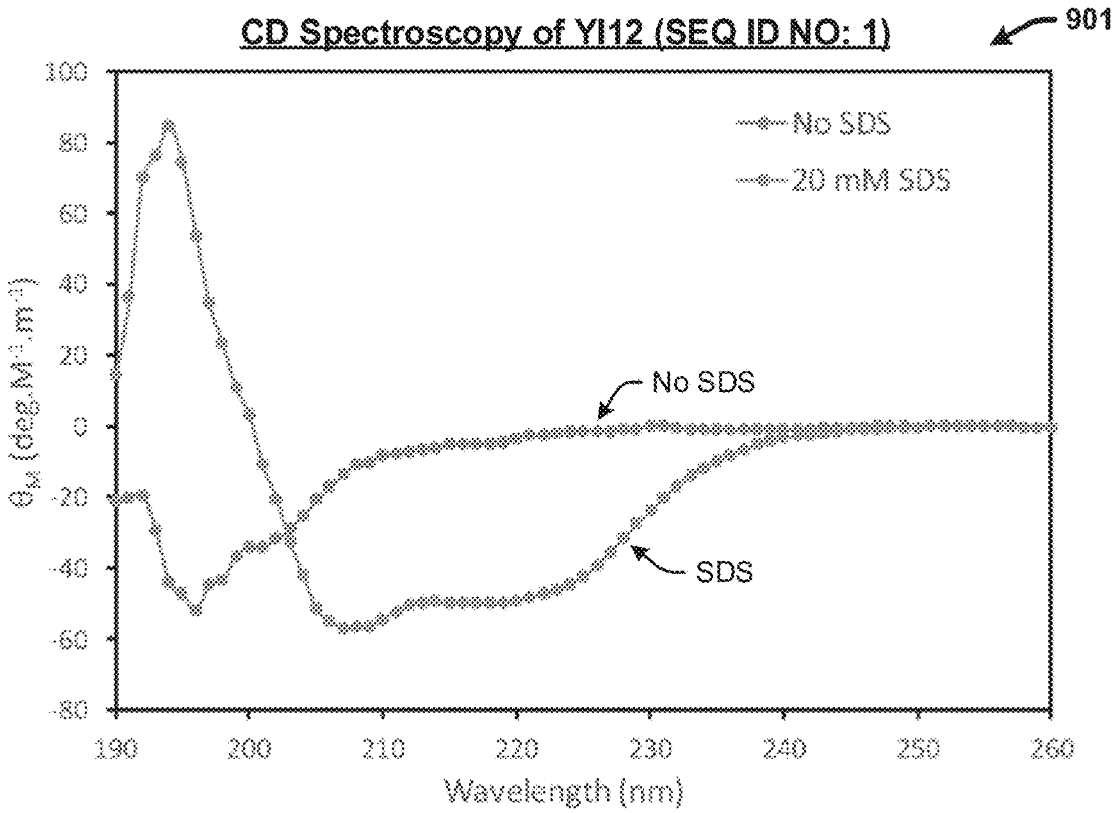
FIGS. 9A and 9B provide graphs illustrating the circular dichroism (CD) spectroscopy of YI12 (SEQ ID NO: 1) and FK13 (SEQ ID NO: 2), respectively.
Figure 9B:
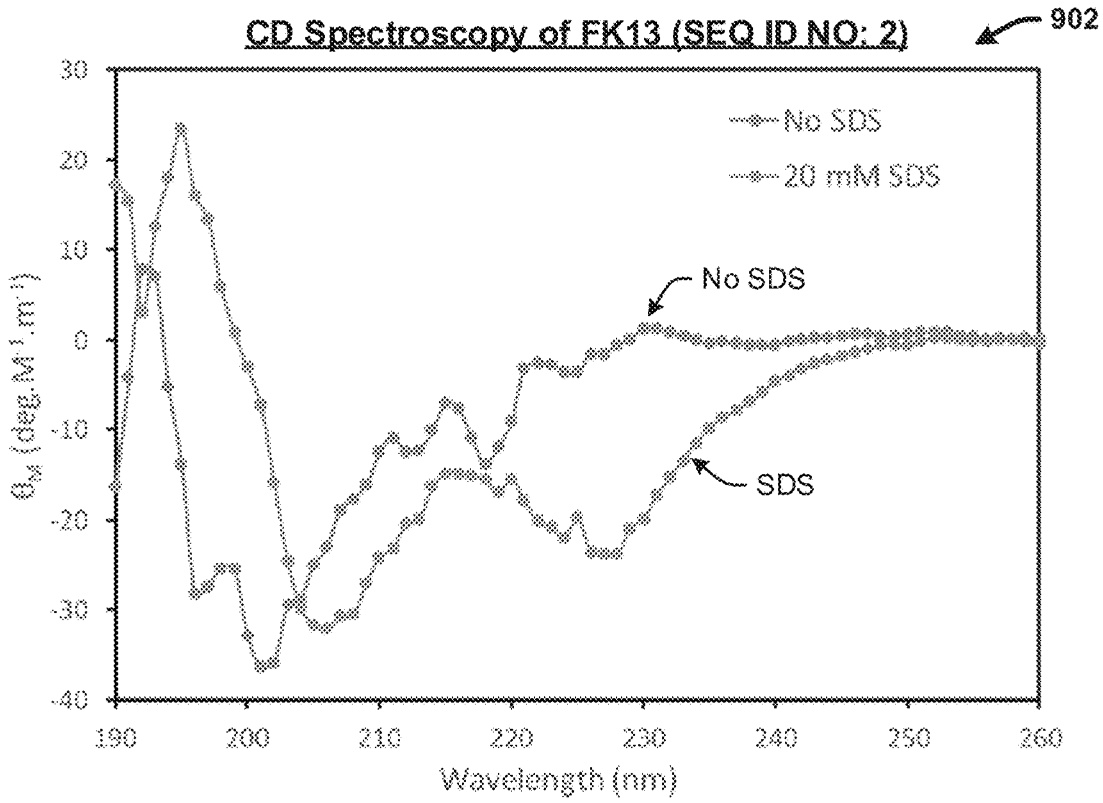

FIGS. 9A and 9B provide graphs illustrating the circular dichroism (CD) spectroscopy of YI12 (SEQ ID NO: 1) and FK13 (SEQ ID NO: 2), respectively. In particular, the structural and mechanical characteristics of YI12 (SEQ ID NO: 1) and FK13 (SEQ ID NO: 2) were further experimentally characterized using CD spectroscopy in deionized DI water (at a DI concentration of 0.5 milligrams per milliliter (mg/ml)) without sodium dodecyl sulfate (SDS) buffer and in presence of 20 mM SDS buffer. The SDS buffer forms micelles in aqueous solution, which mimics the bacterial membrane. Both YI12 (SEQ ID NO: 1) and FK13 (SEQ ID NO: 2) showed a random coil like structure in absence of SDS. When SDS was present, both sequences form an α-helical structure (evident from the 208 nm and 222 nm peaks), consistent with their deep learning predictions and molecular simulations. From the CD spectra, α-helicity of YI12 (SEQ ID NO: 1) appears stronger than that of FK13 (SEQ ID NO: 2), in line with the stronger hydrophobic moment of YI12 (SEQ ID NO: 1).

In summary, the physicochemical analyses of coarse-grained and all-atom simulations and CD spectroscopy together suggest that cationic nature and amphiphilic helical topology are underlying factors inducing antimicrobial nature in YI12 (SEQ ID NO: 1) and FK13 (SEQ ID NO: 2). Taken together, these results illustrate that the current approach is capable of efficiently learning the complex sequence-function relationship in peptides and exploiting that knowledge to generate novel and optimal antimicrobial sequences with broad-spectrum efficacy and low toxicity.

In addition, with reference again to FIG. 4, all-atom (AA) explicit water simulations were performed for both YI12 (SEQ ID NO: 1) and FK13 (SEQ ID NO: 2) in the presence of a lipid membrane starting from an α-helical structure, as seen in CD experiments. Different membrane binding mechanisms were observed for the two sequences. In particular, YI12 (SEQ ID NO: 1) embeds into the membrane using two positively charged Lysine (K) residues close to the C-terminus. On the other hand, FK13 (SEQ ID NO: 2) embeds with the C-terminal Tryptophan (W), with the C-terminal Lysine (K) lying flat on the membrane. These results provide mechanistic insights onto different modes of action adopted by YI12 (SEQ ID NO: 1) and FK13 (SEQ ID NO: 2) during early stages of membrane interaction.

The disclosed CLaSS generated peptides and AMPs (e.g., YI12 (SEQ ID NO: 1) and FK13 (SEQ ID NO: 2)) can be used to in various products to exterminate and/or inhibit growth and/or proliferation of one or more type of bacteria or other pathogens. In certain embodiments the bacterium can comprise Gram positive bacteria and/or a Gram negative bacteria, including (but not limited to): MDR *K. pneumonia, P. aeruginosa, A. baummannii, S. aureus*, and *E. coli*. These products can include medical products, medical product coating, pharmaceutical products, cleaning products and the like. When used as a pharmaceutical product, one or more of the disclosed AMPs can be incorporated into a pharmaceutical formulation using a pharmaceutically acceptable excipient. In some implementations, both YI12 (SEQ ID NO: 1) and FK13 (SEQ ID NO: 2) can be used in combination.

The pharmaceutical product can be administered to a patient and used for the treatment of bacterial infections and other pathogen-based diseases. In certain embodiments the excipient is acceptable for administration to an oral mucosa. In various implementations, the antimicrobial products/pharmaceutical formulations are effective against various types of bacteria, including Gram positive bacteria and Gram negative bacteria. In various embodiments, the antimicrobial products/pharmaceutical formulations are effective against MDR *K. pneumonia, P. aeruginosa, A. baummannii, S. aureus*, and *E. coli*.

Figure 10:
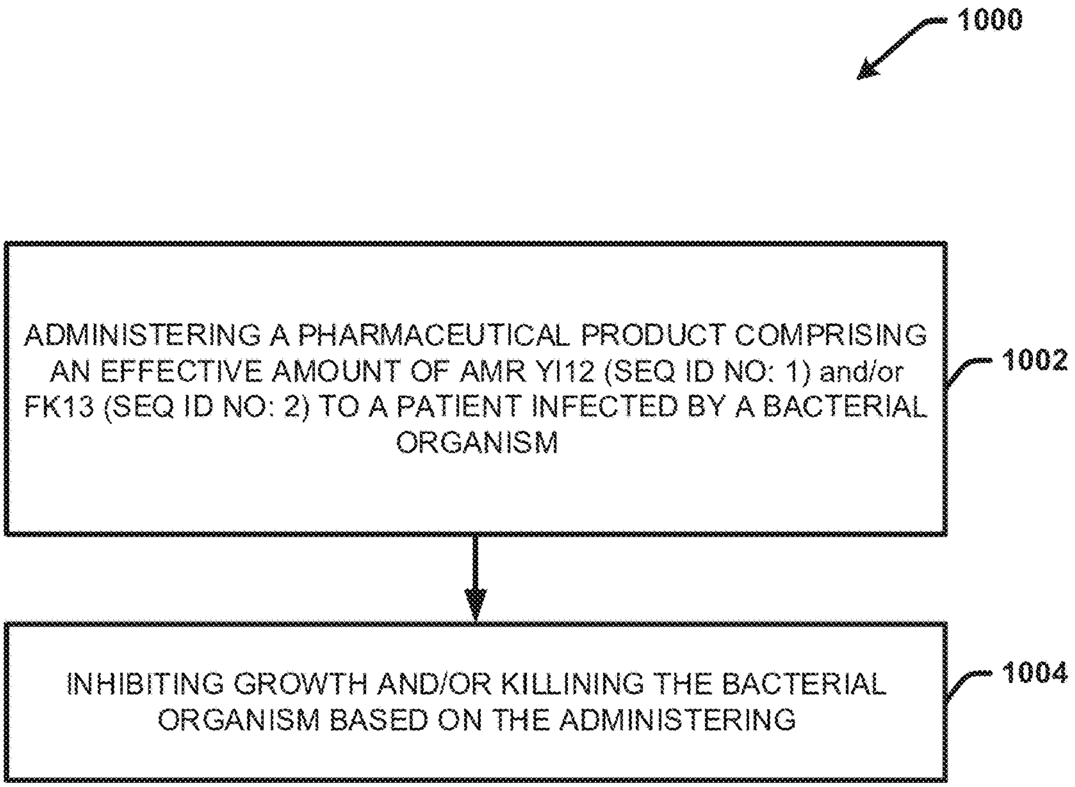
FIG. 10 present an example method for inhibiting the growth and/or proliferation of a bacterium (or other pathogen), in accordance with one or more embodiments of the disclosed subject matter.

FIG. 10 present an example method 1000 for inhibiting the growth and/or proliferation of a bacterium (or other pathogen), in accordance with one or more embodiments of the disclosed subject matter.

Also provided are methods of inhibiting the growth and/or proliferation of a bacterium (or other pathogens). The methods typically involve contacting the bacterium or other pathogen with one or more of the synthetic peptides and/or AMPs described herein, in an amount sufficient to inhibit growth and/or proliferation of the bacterium or other pathogen. In certain embodiments the amount is an amount sufficient to exterminate the bacterium/pathogen. For example, in accordance with method 1000, at 1002, the method can comprise administering a pharmaceutical product comprising an effective amount of AMR YI12 (SEQ ID NO: 1) and/or FK13 (SEQ ID NO: 2) to a patient infected by a bacterial organism. In certain embodiments the bacterial organism can comprise a Gram positive bacterium and/or a Gram negative bacterium, including (but not limited to): MDR *K. pneumonia, P. aeruginosa, A. baummannii, S. aureus*, and *E. coli*. At 1004, the method further comprises inhibiting growth and/or exterminating the bacterial organism based on the administering. In this regard, the effective amount of the AMR can be determined based on the patient, the level of infection of the patient, and the amount of the AMR needed to inhibit growth and/or kill the bacterial organism as determined based on clinical experimentation.

It should be noted that, for simplicity of explanation, in some circumstances the computer-implemented methodologies are depicted and described herein as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts can be required to implement the computer-implemented methodologies in accordance with the disclosed subject matter. In addition, those skilled in the art will understand and appreciate that the computer-implemented methodologies could alternatively be represented as a series of interrelated states via a state diagram or events. Additionally, it should be further appreciated that the computer-implemented methodologies disclosed hereinafter and throughout this specification are capable of being stored on an article of manufacture to facilitate transporting and transferring such computer-implemented methodologies to computers. The term article of manufacture, as used herein, is intended to encompass a computer program accessible from any computer-readable device or storage media.

Figure 11:
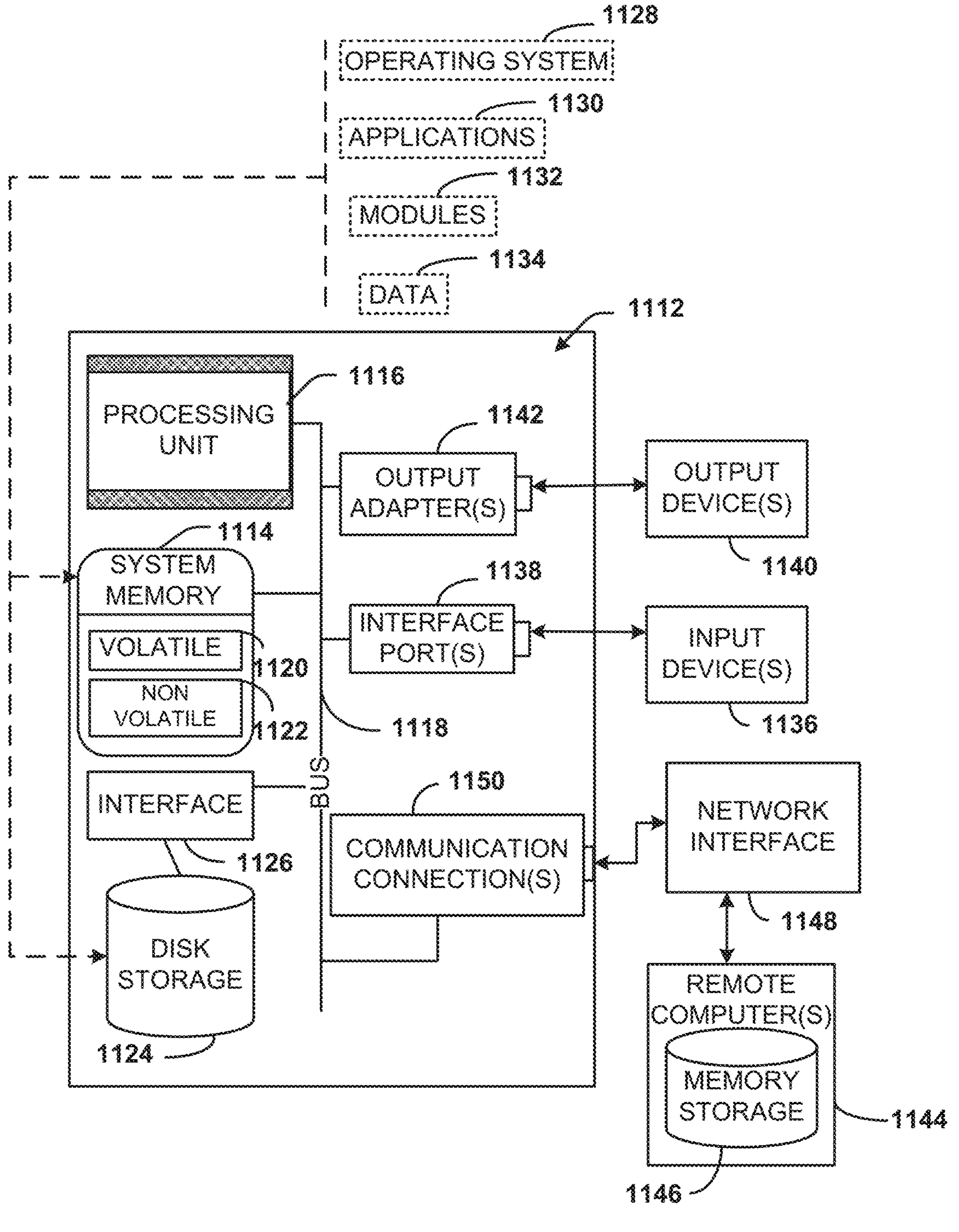
FIG. 11 illustrates a block diagram of an example, non-limiting operating environment in which one or more embodiments described herein can be facilitated.

FIG. 11 can provide a non-limiting context for the various aspects of the disclosed subject matter, intended to provide a general description of a suitable environment in which the various aspects of the disclosed subject matter can be implemented. FIG. 11 illustrates a block diagram of an example, non-limiting operating environment in which one or more embodiments described herein can be facilitated. Repetitive description of like elements employed in other embodiments described herein is omitted for sake of brevity.

With reference to FIG. 11, a suitable operating environment 1100 for implementing various aspects of this disclosure can also include a computer 1112. The computer 1112 can also include a processing unit 1116, a system memory 1114, and a system bus 1118. The system bus 1118 couples system components including, but not limited to, the system memory 1114 to the processing unit 1116. The processing unit 1116 can be any of various available processors. Dual microprocessors and other multiprocessor architectures also can be employed as the processing unit 1116. The system bus 1118 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MCA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire (IEEE 11114), and Small Computer Systems Interface (SCSI).

The system memory 1114 can also include volatile memory 1120 and nonvolatile memory 1122. The basic input/output system (BIOS), containing the basic routines to transfer information between elements within the computer 1112, such as during start-up, is stored in nonvolatile memory 1122. Computer 1112 can also include removable/non-removable, volatile/non-volatile computer storage media. FIG. 11 illustrates, for example, a disk storage 1124. Disk storage 1124 can also include, but is not limited to, devices like a magnetic disk drive, floppy disk drive, tape drive, Jaz drive, Zip drive, LS-100 drive, flash memory card, or memory stick. The disk storage 1124 also can include storage media separately or in combination with other storage media. To facilitate connection of the disk storage 1124 to the system bus 1118, a removable or non-removable interface is typically used, such as interface 1126. FIG. 11 also depicts software that acts as an intermediary between users and the basic computer resources described in the suitable operating environment 1100. Such software can also include, for example, an operating system 1128. Operating system 1128, which can be stored on disk storage 1124, acts to control and allocate resources of the computer 1112.

System applications 1130 take advantage of the management of resources by operating system 1128 through program modules 1132 and program data 1134, e.g., stored either in system memory 1114 or on disk storage 1124. It is to be appreciated that this disclosure can be implemented with various operating systems or combinations of operating systems. A user enters commands or information into the computer 1112 through input device(s) 1136. Input devices 1136 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1116 through the system bus 1118 via interface port(s) 1138. Interface port(s) 1138 include, for example, a serial port, a parallel port, a game port, and a universal serial bus (USB). Output device(s) 1140 use some of the same type of ports as input device(s) 1136. Thus, for example, a USB port can be used to provide input to computer 1112, and to output information from computer 1112 to an output device 1140. Output adapter 1142 is provided to illustrate that there are some output devices 1140 like monitors, speakers, and printers, among other output devices 1140, which require special adapters. The output adapters 1142 include, by way of illustration and not limitation, video and sound cards that provide a means of connection between the output device 1140 and the system bus 1118. It should be noted that other devices and/or systems of devices provide both input and output capabilities such as remote computer(s) 1144.

Computer 1112 can operate in a networked environment using logical connections to one or more remote computers, such as remote computer(s) 1144. The remote computer(s) 1144 can be a computer, a server, a router, a network PC, a workstation, a microprocessor based appliance, a peer device or other common network node and the like, and typically can also include many or all of the elements described relative to computer 1112. For purposes of brevity, only a memory storage device 1146 is illustrated with remote computer(s) 1144. Remote computer(s) 1144 is logically connected to computer 1112 through a network interface 1148 and then physically connected via communication connection 1150. Network interface 1148 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). Communication connection(s) 1150 refers to the hardware/software employed to connect the network interface 1148 to the system bus 1118. While communication connection 1150 is shown for illustrative clarity inside computer 1112, it can also be external to computer 1112. The hardware/software for connection to the network interface 1148 can also include, for exemplary purposes only, internal and external technologies such as, modems including regular telephone grade modems, cable modems and DSL modems, ISDN adapters, and Ethernet cards.

One or more embodiments described herein can be a system, a method, an apparatus and/or a computer program product at any possible technical detail level of integration. The computer program product can include a computer readable storage medium (or media) having computer readable program instructions thereon for causing a processor to carry out aspects of one or more embodiment. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. In this regard, in various embodiments, a computer readable storage medium as used herein can include non-transitory and tangible computer readable storage mediums.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of one or more embodiments can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of one or more embodiments.

Aspects of one or more embodiments are described herein with reference to flowchart illustrations and/or block diagrams of methods, apparatus (systems), and computer program products according to embodiments. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and other devices to function in a particular manner, such that the computer readable storage medium having instructions stored therein comprises an article of manufacture including instructions which implement aspects of the function/act specified in the flowchart and block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and block diagram block or blocks.

The flowchart and block diagrams in the Figures illustrate the architecture, functionality, and operation of possible implementations of systems, methods, and computer program products according to various embodiments described herein. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and flowchart illustration, and combinations of blocks in the block diagrams and flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on one or more computers, those skilled in the art will recognize that this disclosure also can or can be implemented in combination with other program modules. Generally, program modules include routines, programs, components, data structures, etc. that perform particular tasks or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices. For example, in one or more embodiments, computer executable components can be executed from memory that can include or be comprised of one or more distributed memory units. As used herein, the term "memory" and "memory unit" are interchangeable. Further, one or more embodiments described herein can execute code of the computer executable components in a distributed manner, e.g., multiple processors combining or working cooperatively to execute code from one or more distributed memory units. As used herein, the term "memory" can encompass a single memory or memory unit at one location or multiple memories or memory units at one or more locations.

As used in this application, the terms "component," "system," "platform," "interface," and the like, can refer to and can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and a computer. By way of illustration, both an application running on a server and the server can be a component. One or more components can reside within a process or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that can provide specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

The term "facilitate" as used herein is in the context of a system, device or component "facilitating" one or more actions or operations, in respect of the nature of complex computing environments in which multiple components and/or multiple devices can be involved in some computing operations. Non-limiting examples of actions that may or may not involve multiple components and/or multiple devices comprise transmitting or receiving data, establishing a connection between devices, determining intermediate results toward obtaining a result (e.g., including employing ML and/or AI techniques to determine the intermediate results), etc. In this regard, a computing device or component can facilitate an operation by playing any part in accomplishing the operation. When operations of a component are described herein, it is thus to be understood that where the operations are described as facilitated by the component, the operations can be optionally completed with the cooperation of one or more other computing devices or components, such as, but not limited to: sensors, antennae, audio and/or visual output devices, other devices, etc.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches, and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A synthetic peptide comprising twelve, natural amino acids in length and the amino acid sequence YLRLIRYMAKMI (SEQ ID NO: 1), wherein the synthetic peptide has antimicrobial activity.

2. The synthetic peptide of claim 1, further comprising a terminal amide with formula CONH2, resulting in the synthetic peptide having the sequence YLRLIRYMAKMI-CONH2 (SEQ ID NO: 1 —CONH2).

3. The synthetic peptide of claim 1, wherein the synthetic peptide has the antimicrobial activity against Gram negative bacteria and Gram positive bacteria.

4. The synthetic peptide of claim 1, wherein the synthetic peptide has the antimicrobial activity against multi-medication resistant *Klebsiella pneumonia.*

5. The synthetic peptide of claim 1, wherein the synthetic peptide has the antimicrobial activity against bacteria selected from the group consisting of: *Pseudomonas aeruginosa, Acinetobacter baummannii, Staphylococcus aureus,* and *Escherichia coli.*

6. The synthetic peptide of claim 1, wherein a minimum inhibitory concentration value of the synthetic peptide with regards to bacteria is less than a median lethal dose value of the synthetic peptide.

7. The synthetic peptide of claim 1, wherein the synthetic peptide exhibits low toxicity as measured by a 50% lethal dose ($LD_{50}$) concentration in mice of 182 milligrams per kilogram (mg/kg).

8. The synthetic peptide of claim 1, wherein the synthetic peptide was designed using one or more artificial intelligence techniques.

9. A synthetic peptide comprising thirteen, natural amino acids in length and the amino acid sequence FPLTWLKWWKWKK (SEQ ID NO: 2) wherein the synthetic peptide has antimicrobial activity.

10. The synthetic peptide of claim 9, further comprising a terminal amide with formula CONH2, resulting in the synthetic peptide having the sequence FPLTWLKWWKWKK-CONH2.

11. The synthetic peptide of claim 9, wherein the synthetic peptide has the antimicrobial activity against Gram negative bacteria and Gram positive bacteria.

12. The synthetic peptide of claim 9, wherein the synthetic peptide has the antimicrobial activity against multi-medication resistant *Klebsiella pneumonia.*

13. The synthetic peptide of claim 9, wherein the synthetic peptide has the antimicrobial activity against bacteria selected from the group consisting of: *Pseudomonas aeruginosa, Acinetobacter baummannii, Staphylococcus aureus,* and *Escherichia coli.*

14. The synthetic peptide of claim 9, wherein the . . . as measured by a 50% lethal dose ($LD_{50}$) concentration in mice of 158 milligrams per kilogram (mg/kg).

15. The synthetic peptide of claim 9, wherein the synthetic peptide was designed using one or more artificial intelligence techniques.

\* \* \* \* \*

SEQUENCE LISTING

```
<160> NUMBER OF SEQ ID NOS: 20

<210> SEQ ID NO 1
<211> LENGTH: 12
<212> TYPE: PRT
<213> ORGANISM: Artificial Sequence
<220> FEATURE:
<223> OTHER INFORMATION: synthetic antimicrobial peptide designed using
      artificial intelligence

<400> SEQUENCE: 1

Tyr Leu Arg Leu Ile Arg Tyr Met Ala Lys Met Ile
1               5                   10


<210> SEQ ID NO 2
<211> LENGTH: 13
<212> TYPE: PRT
<213> ORGANISM: Artificial Sequence
<220> FEATURE:
<223> OTHER INFORMATION: synthetic antimicrobial peptide designed using
      artificial intelligence

<400> SEQUENCE: 2

Phe Pro Leu Thr Trp Leu Lys Trp Trp Lys Trp Lys Lys
1               5                   10


<210> SEQ ID NO 3
<211> LENGTH: 12
<212> TYPE: PRT
<213> ORGANISM: Artificial Sequence
<220> FEATURE:
<223> OTHER INFORMATION: synthetic antimicrobial peptide designed using
```

-continued

```
      artificial intelligence

<400> SEQUENCE: 3

His Ile Leu Arg Met Arg Ile Arg Gln Met Met Thr
1               5                   10


<210> SEQ ID NO 4
<211> LENGTH: 13
<212> TYPE: PRT
<213> ORGANISM: Artificial Sequence
<220> FEATURE:
<223> OTHER INFORMATION: synthetic antimicrobial peptide designed using
      artificial intelligence

<400> SEQUENCE: 4

Ile Leu Leu His Ala Ile Leu Gly Val Arg Lys Lys Leu
1               5                   10


<210> SEQ ID NO 5
<211> LENGTH: 13
<212> TYPE: PRT
<213> ORGANISM: Artificial Sequence
<220> FEATURE:
<223> OTHER INFORMATION: synthetic antimicrobial peptide designed using
      artificial intelligence

<400> SEQUENCE: 5

Tyr Arg Ala Ala Met Leu Arg Arg Gln Tyr Met Met Thr
1               5                   10


<210> SEQ ID NO 6
<211> LENGTH: 12
<212> TYPE: PRT
<213> ORGANISM: Artificial Sequence
<220> FEATURE:
<223> OTHER INFORMATION: synthetic antimicrobial peptide designed using
      artificial intelligence

<400> SEQUENCE: 6

His Ile Arg Leu Met Arg Ile Arg Gln Met Met Thr
1               5                   10


<210> SEQ ID NO 7
<211> LENGTH: 13
<212> TYPE: PRT
<213> ORGANISM: Artificial Sequence
<220> FEATURE:
<223> OTHER INFORMATION: synthetic antimicrobial peptide designed using
      artificial intelligence

<400> SEQUENCE: 7

His Ile Arg Ala Met Arg Ile Arg Ala Gln Met Met Thr
1               5                   10


<210> SEQ ID NO 8
<211> LENGTH: 14
<212> TYPE: PRT
<213> ORGANISM: Artificial Sequence
<220> FEATURE:
<223> OTHER INFORMATION: synthetic antimicrobial peptide designed using
      artificial intelligence

<400> SEQUENCE: 8

Lys Thr Leu Ala Gln Leu Ser Ala Gly Val Lys Arg Trp His
1               5                   10


<210> SEQ ID NO 9
```

-continued

```
<211> LENGTH: 13
<212> TYPE: PRT
<213> ORGANISM: Artificial Sequence
<220> FEATURE:
<223> OTHER INFORMATION: synthetic antimicrobial peptide designed using
      artificial intelligence

<400> SEQUENCE: 9

His Ile Leu Arg Met Arg Ile Arg Gln Gly Met Met Thr
1               5                   10


<210> SEQ ID NO 10
<211> LENGTH: 13
<212> TYPE: PRT
<213> ORGANISM: Artificial Sequence
<220> FEATURE:
<223> OTHER INFORMATION: synthetic antimicrobial peptide designed using
      artificial intelligence

<400> SEQUENCE: 10

His Arg Ala Ile Met Leu Arg Ile Arg Gln Met Met Thr
1               5                   10


<210> SEQ ID NO 11
<211> LENGTH: 14
<212> TYPE: PRT
<213> ORGANISM: Artificial Sequence
<220> FEATURE:
<223> OTHER INFORMATION: synthetic antimicrobial peptide designed using
      artificial intelligence

<400> SEQUENCE: 11

Glu Tyr Leu Ile Glu Val Arg Glu Ser Ala Lys Met Thr Gln
1               5                   10


<210> SEQ ID NO 12
<211> LENGTH: 14
<212> TYPE: PRT
<213> ORGANISM: Artificial Sequence
<220> FEATURE:
<223> OTHER INFORMATION: synthetic antimicrobial peptide designed using
      artificial intelligence

<400> SEQUENCE: 12

Gly Leu Ile Thr Met Leu Lys Val Gly Leu Ala Lys Val Gln
1               5                   10


<210> SEQ ID NO 13
<211> LENGTH: 12
<212> TYPE: PRT
<213> ORGANISM: Artificial Sequence
<220> FEATURE:
<223> OTHER INFORMATION: synthetic antimicrobial peptide designed using
      artificial intelligence

<400> SEQUENCE: 13

Tyr Gln Leu Leu Arg Ile Met Arg Ile Asn Ile Ala
1               5                   10


<210> SEQ ID NO 14
<211> LENGTH: 13
<212> TYPE: PRT
<213> ORGANISM: Artificial Sequence
<220> FEATURE:
<223> OTHER INFORMATION: synthetic antimicrobial peptide designed using
      artificial intelligence

<400> SEQUENCE: 14
```

Val Arg Trp Ile Glu Tyr Trp Arg Glu Lys Trp Arg Thr
1 5 10

<210> SEQ ID NO 15
<211> LENGTH: 14
<212> TYPE: PRT
<213> ORGANISM: Artificial Sequence
<220> FEATURE:
<223> OTHER INFORMATION: synthetic antimicrobial peptide designed using artificial intelligence

<400> SEQUENCE: 15

Leu Ile Gln Val Ala Pro Leu Gly Arg Leu Leu Lys Arg Arg
1 5 10

<210> SEQ ID NO 16
<211> LENGTH: 11
<212> TYPE: PRT
<213> ORGANISM: Artificial Sequence
<220> FEATURE:
<223> OTHER INFORMATION: synthetic antimicrobial peptide designed using artificial intelligence

<400> SEQUENCE: 16

Tyr Gln Leu Arg Leu Ile Met Lys Tyr Ala Ile
1 5 10

<210> SEQ ID NO 17
<211> LENGTH: 12
<212> TYPE: PRT
<213> ORGANISM: Artificial Sequence
<220> FEATURE:
<223> OTHER INFORMATION: synthetic antimicrobial peptide designed using artificial intelligence

<400> SEQUENCE: 17

His Arg Ala Leu Met Arg Ile Arg Gln Cys Met Thr
1 5 10

<210> SEQ ID NO 18
<211> LENGTH: 12
<212> TYPE: PRT
<213> ORGANISM: Artificial Sequence
<220> FEATURE:
<223> OTHER INFORMATION: synthetic antimicrobial peptide designed using artificial intelligence

<400> SEQUENCE: 18

Gly Trp Leu Pro Thr Glu Lys Trp Arg Lys Leu Cys
1 5 10

<210> SEQ ID NO 19
<211> LENGTH: 12
<212> TYPE: PRT
<213> ORGANISM: Artificial Sequence
<220> FEATURE:
<223> OTHER INFORMATION: synthetic antimicrobial peptide designed using artificial intelligence

<400> SEQUENCE: 19

Tyr Gln Leu Arg Leu Met Arg Ile Met Ser Arg Ile
1 5 10

<210> SEQ ID NO 20
<211> LENGTH: 9
<212> TYPE: PRT
<213> ORGANISM: Artificial Sequence
<220> FEATURE:

-continued

```
<223> OTHER INFORMATION: synthetic antimicrobial peptide designed using
      artificial intelligence

<400> SEQUENCE: 20

Leu Arg Pro Ala Phe Lys Val Ser Lys
1               5
```